US010905685B2

(12) United States Patent
Foster et al.

(10) Patent No.: US 10,905,685 B2
(45) Date of Patent: *Feb. 2, 2021

(54) INTRATHECAL HYDROMORPHONE SOLUTIONS HAVING IMPROVED STABILITY

(71) Applicant: PIRAMAL CRITICAL CARE LIMITED, West Drayton (GB)

(72) Inventors: John J. Foster, St. Paul, MN (US); Thomas R. Prentice, St. Paul, MN (US)

(73) Assignee: Piramal Critical Care, Inc., Bethlehem, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/019,828

(22) Filed: Sep. 6, 2013

(65) Prior Publication Data

US 2014/0005219 A1    Jan. 2, 2014

Related U.S. Application Data

(63) Continuation-in-part of application No. 13/787,042, filed on Mar. 6, 2013, now Pat. No. 9,155,734.

(60) Provisional application No. 61/607,774, filed on Mar. 7, 2012.

(51) Int. Cl.
*A61K 31/485* (2006.01)
*A61K 9/00* (2006.01)
*A61K 9/08* (2006.01)

(52) U.S. Cl.
CPC .......... *A61K 31/485* (2013.01); *A61K 9/0019* (2013.01); *A61K 9/0085* (2013.01); *A61K 9/08* (2013.01)

(58) Field of Classification Search
CPC .. A61K 31/485; A61K 9/0019; A61K 9/0085; A61K 9/08; A61P 25/04
See application file for complete search history.

(56) References Cited

U.S. PATENT DOCUMENTS

| | | | |
|---|---|---|---|
| 6,512,117 B1 * | 1/2003 | Harclerode et al. | 546/45 |
| 6,589,960 B2 | 7/2003 | Harclerode et al. | |
| 8,188,048 B2 | 5/2012 | Lewis | |
| 8,268,774 B2 | 9/2012 | Ellis et al. | |
| 8,410,129 B2 | 4/2013 | Brooks-Korn | |
| 8,461,171 B2 | 6/2013 | Holaday et al. | |
| 9,155,734 B2 | 10/2015 | Foster | |
| 2003/0045720 A1 | 3/2003 | Harclerode et al. | |
| 2004/0102476 A1 | 5/2004 | Chan et al. | |
| 2006/0235039 A1 * | 10/2006 | Lorimer | C07D 489/04 514/282 |
| 2010/0216842 A1 | 8/2010 | Nabeta et al. | |
| 2012/0270848 A1 | 10/2012 | Mannion et al. | |
| 2012/0310140 A1 | 12/2012 | Kramer et al. | |
| 2013/0041241 A1 | 2/2013 | Felts et al. | |
| 2013/0096066 A1 | 4/2013 | Ellis et al. | |

FOREIGN PATENT DOCUMENTS

| | | |
|---|---|---|
| EP | 2446882 | 5/2012 |
| WO | 9711681 | 4/1997 |
| WO | WO2005032556 A1 * | 4/2005 |
| WO | WO200722609 A1 * | 3/2007 |
| WO | 2012075337 A2 | 6/2012 |
| WO | 2013063263 A1 | 5/2013 |
| WO | 2013071138 A1 | 5/2013 |
| WO | 2013/134362 A1 | 9/2013 |
| WO | 2014/137385 A1 | 9/2014 |

OTHER PUBLICATIONS

Hildenbrand et al. Stability and Compatibility of Hydromorphone Hydrochloride in an Implantable Infusion System. J. of Pain and Symptom Management. 2001, vol. 22, pp. 1042-1047.*
Dilaudid-HP® Injection (hydromorphone hydrochloride) full prescription description (Oct. 2011, pp. 1-18). [online] [retrieved on Mar. 31, 2014]. Retrieved from the Internet: <URL:http://dailymed.nlm.nih.gov/dailymed/lookup.cfm?setid=c88f81ac-1643-4c08-ae2c-63cbe956db7e.*
Dilaudid Injection [online] Retrieved on Dec. 26, 2018, Retrieved from the internet, <url: https://www.accessdata.fda.gov/drugsatfda_docs/label/2011/019034s021lbl.pdf> (Year: 2011).*
Trissel et al., "Physical and Chemical Stability of Hydromorphone Hydrochloride 1.5 and 80 mg/ml packaged in plastic syringes"' Intl Journal of Pharma. Compounding; Jan. 2002; pp. 74-76.
Anonymous: "USP NF, The official compendia of standards", 2002, US Pharmacopeial Convention; p. 1579.
Williams et al., "Formulating Poorly Water Soluble Drugs", 2012, Springer, vol. 3; p. 230.
Gennaro, "Remington: the science and practice of pharmacy", 2000, Lippincott Williams & Wilkins, pp. 770-771; pp. 815-817.
Dilaudid-HP Injection Package Insert.
Boswell et al, "Interventional Techniques: Evidence-based Practice Guidelines in the Management of Chronic Spinal Pain"; Pain Physician 2007; 10:7-111.
Deer et al, "Polyanalgesic Consensus Conference 2007: Recommendations for the Management of Pain by Intrathecal (Intraspinal) Drug Delivery: Report of an Interdisciplinary Expert panel"; Neuromodulation: Technology at the Neural Interface; Intl Neuromodulation Society; vol. 10; No. 4, 2007pp. 300-328.

(Continued)

*Primary Examiner* — Sahar Javanmard
(74) *Attorney, Agent, or Firm* — Merchant & Gould P.C.

(57) ABSTRACT

The present disclosure relates generally to a pharmaceutical solution comprising hydromorphone or a pharmaceutically acceptable salt thereof that is substantially free of buffer and optionally one or more other additives. The pharmaceutically acceptable salt may be hydromorphone hydrochloride. Also disclosed are methods for the manufacture and use of the solution.

14 Claims, 2 Drawing Sheets

(56) References Cited

OTHER PUBLICATIONS

Anderson et al. "Intrathecal Hydromorphone for Chronic Nonmalignant Pain: A Retrospective Study"; American Academy of Pain Medicine; vol. 2; No. 4, 2001; pp. 287-297.
Allen et al.; "Opiate Pharmacology of Intrathecal Granulomas"; the American Society of Anesthesiology 2006; 105: 590-8.
Smith et al., "Intrathecal Drug Delivery"; Pain Physician Journal 2008; Opioid Special Issue; 11; S89-S104.
Roy et al, "Solubility and Related Physicochemical Properties of Narcotic Analgesics"; Pharmaceutical Research, vol. 5, No. 9, 1988; 580-586.
Ramsey et al., "Intrathecal Granuloma in a Patient Receiving High Dose Hydromorphone"; Pain Physician Journal; 2008; 11:3:369-373.
Johansen et al.; "Continuous Intrathecal Infusion of Hydromorphone: Safety in the Sheep Model and Clinical Implications"; American Academy of Pain Medicine; vol. 5; No. 1; 2004; pp. 14-25.
Du Pen et al.; "Intrathecal Hydromorphone for Intractable Nonmalignant Pain: A Retrospective Study"; American Academy of Pain Medicine; vol. 7; No. 1; 2006; pp. 10-15.
Ahern, et al., "Safety and Efficacy of Low-dose Ketamine Added to a Hydromorphone Titration Protocol for Emergency Department Patients With Acute Severe Pain," Annals of Emergency Medicine, 2012, vol. 60, No. 4S, p. S53, Abstract No. 146.
Gagnon, et al. "Tremors and Agitation Following Low-Dose Intravenous Hydromorphone Administration in a Patient with Kidney Dysfunction," Annals of Pharmacotherapy, 2013, vol. 47, pp. e34.
Oldenmenger, et al., "Efficacy of opioid rotation to continuous parenteral hydromorphone in advanced cancer patients failing on other opioids," Support. Care Cancer, 2012, vol. 20, pp. 1639-1647.
Chang, et al., "Randomized Clinical Trial of an Intravenous Hydromorphone Titration Protocol versus Usual Care for Management of Acute Pain in Older Emergency Department Patients," Drugs Aging, published online on Jul. 12, 2013, DOI 10.1007/s40266-013-0103-y.
Guzman, et al., "Evaluation of thermal antinociceptive effects after intramuscular administration of hydromorphone hydrochloride to American kestrels (Falco sparverius)," Am. J. Vet. Res., 2013, vol. 74, pp. 817-822.
Sun, et al., "Determination of hydromorphone in human plasma by a sensitive RP-HPLC-ESI-MS method and its application to a clinical pharmacokinetic study in postoperative patients after low dose intravenous administration with infusion pump," J. Pharm. Biomed. Anal., 2012, vol. 61, pp. 15-21.
Chang, et al., "Randomized Clinical Trial of the 2 mg Hydromorphone Bolus Protocol Versus the '1+1' Hydromorphone Titration Protocol in Treatment of Acute, Severe Pain in the First Hour of Emergency Department Presentation," Ann. Emerg. Med., May 20, 2013 (corrected proof).
Hayek, et al., "Analysis of long term effectiveness of continuous intrathecal infusion of hydromorphone and bupivacaine in combination with PTM," Pain Practice, 2012, vol. 12, Supp. S1, pp. 172-173, No. PP641.
Lee, et al., "Intrathecal hydromorphone added to hyperbaric bupivacaine for postoperative pain relief after knee arthroscopic surgery: a prospective, randomised controlled trial," Eur. J. Anaesthesiol., 2012, vol. 29, pp. 17-21.
Xia, et al., "Lack of Association Between Body Mass Index Clinical Response to 1 mg Intravenous Hydromorphone," Academic Emergency Medicine, May 2013, vol. 20, No. 5, Suppl. 1, pp. S226-S227, No. 565.
Butt, "Morphologic Changes Associated with Intrathecal Catheters for Direct Delivery to the Central Nervous System in Preclinical Studies," Toxicology Pathology, 2011, vol. 39, pp. 213-219 (published online Dec. 2010).
Knight, et al., "Implantable intrathecal pumps for chronic pain: highlights and updates," Croation Medical Journal, 2007, vol. 48(1), pp. 22-34.
Hildebrand, et al., "Stability, compatibility, and safety of intrathecal bupivacaine administered chronically via an implantable delivery system," Clinical Journal of Pain, 2001, vol. 17(3), pp. 239-244.
Murray, et al., "Hydromorphone," Journal of Pain and Symptom Management, 2005, vol. 29 (5 Suppl.), pp. S57-S66.
Sarhill, et al., "Hydromorphone: pharmacology and clinical applications in cancer patients," Supportive Care in Cancer, 2001, vol. 9, No. 2, pp. 84-96.
Quigley, "Hydromorphone for acute and chronic pain," Cochrane Database of Systematic Reviews, 2002, Issue 1, Art. No. CD003447.
Stearns, et al., "Intrathecal drug delivery for the management of cancer pain: a multidisciplinary consensus of best clinical practices," J. of Supportive Oncology, 2005, vol. 3(6), pp. 399-408.
"Intrathecal Drug Delivery for the Management of Pain and Spasticity in Adults, Recommendations for Best Clinical Practice," British Pain Society, Aug. 2008.
Newsome, et al., "Intrathecal analgesia for refractory cancer pain," Current Pain and Headache Reports, 2008, vol. 12(4), pp. 249-256.
Bennett, et al., "Intrathecal administration of an NMDA or a non-NMDA receptor antagonist reduces mechanical but not thermal allodynia in a rodent model of chronic central pain after spinal cord injury," Brain Research, 2000, vol. 859 (1), pp. 72-82.
Chang, et al., "Safety and efficacy of hydromorphone as an analgesic alternative to morphine in acute pain: a randomized clinical trial," Annals of Emergency Medicine, 2006, vol. 48(2), pp. 164-172.
Coombs, et al., "Continuous intrathecal hydromorphone and clonidine for intractable cancer pain," Journal of Neurosurgery, 1986, vol. 64(6), pp. 890-894.
Kedlaya, et al., "Epidural and intrathecal analgesia for cancer pain," Best Practice and Research Clinical Anaesthesiology, 2002, vol. 16(4), pp. 651-665.
Smith, et al., "Intrathecal drug delivery," Pain Physician, 2008, vol. 11 (2 Suppl), pp. S89-5104.
Turner, et al., "Programmable intrathecal opioid delivery systems for chronic noncancer pain: a systematic review of effectiveness and complications," Clinical Journal of Pain, 2007, vol. 23(2), pp. 180-195.
Raffaeli, et al., "Intraspinal therapy for the treatment of chronic pain: a review of the literature between 1990 and 2005 and suggested protocol for its rational and safe use," Neuromodulation, 2006, vol. 9(4), pp. 290-308.
Saulino, "Successful reduction of neuropathic pain associated with spinal cord injury via of a combination of intrathecal hydromorphone and ziconotide: a case report," Spinal Cord, 2007, vol. 45(11), pp. 749-752.
Chiarella et al., "A Comparison of Intrathecal Hydromorphone with Morphine for Post-Operative Analgesia and Side Effects in Total Joint Arthroplasty," Anesthesiology and Pain Medicine, University of Alberta Hospital, Edmonton, Alberta, Canada, 2002.
Tobias, "A review of intrathecal and epidural analgesia after spinal surgery in children," Anesthesia and Analgesia, 2004, vol. 98(4), pp. 956-965.
McMillan, et al., "Catheter-associated masses in patients receiving intrathecal analgesic therapy," Anesthesia and Analgesia, 2003, vol. 96(1), pp. 186-190.
Coffey, et al., "Inflammatory mass lesions associated with intrathecal drug infusion catheters: report and observations on 41 patients," Neurosurgery, 2002, vol. 50 (1), pp. 78-86.
International Search Report dated Nov. 26, 2013 from related international application No. PCT/US2013/058519, 3 pgs.
International Search Report dated Jun. 11, 2013 from related international application No. PCT/US2013/029328, 2 pgs.
Office action dated Aug. 19, 2013 from related U.S. Appl. No. 13/787,042, 9 pgs.
Office action dated Mar. 21, 2014 from related U.S. Appl. No. 13/787,042, 18 pgs.
Office action dated Nov. 6, 2014 from related U.S. Appl. No. 13/787,042, 20 pgs.
Office action dated Jul. 18, 2016 from related U.S. Appl. No. 14/834,536, 21 pgs.
Office action dated Jan. 30, 2017 from related U.S. Appl. No. 14/834,536, 12 pgs.

(56) References Cited

OTHER PUBLICATIONS

Preliminary Report on Patentability dated Jun. 27, 2014 related international Application No. PCT/US2013/029328, 9 pgs.
Purdue Pharma, L.P., Full Prescribing Information, Oct. 2011 (http://app.purduepharma.com/xmlpublishing/pl.aspx?id+dl)., 23 pgs.
Hildenbrand, Stability and Compatibility of Hydromorphone Hydrochloride in an Implantable Infusion System, J. of Pain and Symptom Mangement, 2001, vol. 22, pp. 1042-1047.
Office action dated Jul. 5, 2016 from related CA Application No. 2,865,815, 3 pgs.
Notice of Allowance dated Oct. 24, 2016 from related CA Application No. 2,865,815, 1 pg.
Office action dated Mar. 8, 2016 from related CN Application No. 201380021041.2, 10 pgs.
Office action dated Aug. 15, 2016 from related CN Application No. 201380021041.2, 6 pgs.
Notification of Decision to Grant dated Feb. 6, 2017 from related CN Application No. 201380021041.2, 3 pgs.
Office action dated Apr. 12, 2016 from related JP Application No. 2014-561072, 5 pgs.
Khondkar, Chemical Stability of Hydromorphone Hydrochloride in Patient-Controlled Analgesia Injector, Int J Pharm Compd, 2010, vol. 14, No. 2, pp. 160-164.
Office action dated Sep. 13, 2016 from related JP Application No. 2014-561072, 4 pgs.
Notice of Allowance dated Dec. 28, 2016 from related JP Application No. 2014-561072, 7 pgs.
Office action dated Jul. 28, 2016 from related KR Application No. 10-2014-7028030, 1 pg.
Notice of Allowance dated Jan. 3, 2017 from related KR Application No. 10-2014-7028030, 1 pg.
Examination Report dated Dec. 21, 2015 from related European Application No. 13 713 600.8, 4 pgs.
The International Pharmacopoeia, 5.8 Methods of sterilization, Fifth Edition, 2015, 3 pgs.

* cited by examiner

INTRATHECAL HYDROMORPHONE SOLUTIONS HAVING IMPROVED STABILITY

CROSS REFERENCE TO RELATED APPLICATIONS

This application is a continuation-in-part of prior U.S. patent application Ser. No. 13/787,042, filed Mar. 6, 2013, which claims the benefit of priority of U.S. Provisional Application No. 61/607,774, filed Mar. 7, 2012.

BACKGROUND OF THE DISCLOSURE

The present disclosure relates generally to a sterile solution of hydromorphone and/or one or more pharmaceutically acceptable salts thereof that is substantially free of buffer and optionally one or more other additives. For example, in one aspect, the present disclosure relates to a sterile hydromorphone hydrochloride solution that is substantially free of buffer and other additives.

Hydromorphone hydrochloride is a narcotic analgesic, and one of its principle uses is the relief of pain. It is a semi-synthetic μ-opioid agonist. There is no intrinsic limit to the analgesic effect of hydromorphone hydrochloride; like morphine, adequate doses will relieve even the most severe pain. Hydromorphone is the generic (USAN) name (USP Dictionary of USAN and International Drug Names 2003) for 4,5-α-epoxy-3-hydroxy-17-methyl morphinan-6-one, a derivative of morphine. Its structural formula is:

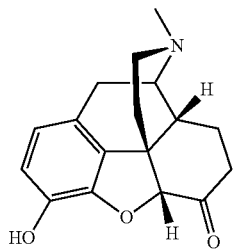

Presently, intrathecal hydromorphone hydrochloride is commercially available for injection in 10 mg/ml solutions in a preservative-free formula containing 0.2% sodium citrate and 0.2% of a citric acid solution.

Hydromorphone is used in medicine as an alternative to morphine and diacetylmorphine for analgesia and as a second- or third-line narcotic antitussive (cough suppressant) for cases of dry, painful, paroxysmal coughing resulting from continuing bronchial irritation after influenza and other ailments, inhalation of fungus and other causes, and is generally regarded to be the strongest of the latter class of drugs, and was developed shortly after another powerful antitussive, heroin, was removed from clinical use for this purpose in most of the world and in many countries banned outright.

The hydrogenation of morphine resulting in the formation of hydromorphone results in a drug with higher lipid solubility and ability to cross the blood-brain barrier and therefore more rapid and complete central nervous system penetration, with the result that hydromorphone is somewhat faster-acting and about eight times stronger than morphine and about three times stronger than heroin on a milligram basis. The effective morphine to hydromorphone conversion ratio can vary from patient to patient by a significant amount with relative levels of some liver enzymes being the main cause; the normal human range appears to be from 8:1 to a little under 4:1. It is not uncommon, for example, for the 8-mg tablet to have an effect similar to 30 mg of morphine sulfate or a similar morphine preparation.

The currently available hydromorphone hydrochloride solutions all contain buffer. The buffer is often added to a composition to regulate the pH and/or aid in the stability of the compound in solution. The addition of buffer can lead to potential complications, such as toxicity or other side effects, allergic responses and/or granuloma formation. Further, the use of less or no buffer would decrease the costs of producing the pharmaceutical composition and reduce manufacturing complexity. Currently available hydromorphone hydrochloride solutions also have not been approved for intrathecal use. Accordingly, there is a need for a hydromorphone hydrochloride solution that does not contain buffer, and is suitable for intrathecal use. Surprisingly, it has been found that hydromorphone hydrochloride, as well as other hydromorphone salts, in water do not require buffering agents to maintain stability over time.

Additionally, there has been increasing interest recently in the regulation of the cerebrospinal fluid (CSF) pH. Part of this interest stems from the fact that the extracellular fluid (ECF) pH in the brain serves as an important regulator of pulmonary ventilation and a major determinant of cerebral blood flow. Furthermore, since the CSF pH has been shown to be subject to a considerable degree of homeostatic control in a variety of conditions which change the acid-base status of blood, many attempts have been made to unravel the physiological mechanisms which are responsible for this control. Finally, since the acid-base metabolism of the cerebral compartments (including the ECF) may influence cerebral function to a significant degree, the CSF pH and the mechanisms which regulate it have become of concern to neurologists and neurosurgeons. CSF normally has a pH near 7.3. Since intrathecal delivery of hydromorphone hydrochloride is direct injection into the CSF, and it is desirable to keep the pH of the resulting CSF—hydromorphone solution mixture as close to 7.3 as possible, injection of a hydromorphone hydrochloride formulation with a pH near 7.3 is appealing. Advantageously, the pH of the formulation without buffer is closer to the natural physiological pH of CSF than the formulation containing buffer (5.0 vs. 4.1).

BRIEF DESCRIPTION OF THE DISCLOSURE

In one aspect, the present disclosure is directed to a sterile pharmaceutical solution comprising hydromorphone, a pharmaceutically acceptable salt(s) thereof, or combinations thereof, wherein the solution is substantially free of buffer and optionally one or more other additives. In one particular embodiment, the solution comprises hydromorphone hydrochloride.

Another aspect of the present disclosure is a sterile pharmaceutical solution consisting essentially of hydromorphone and/or a pharmaceutically acceptable salt(s) thereof and water. In one particular embodiment, the pharmaceutically acceptable salt is hydromorphone hydrochloride.

Yet another aspect of the present disclosure is a sterile pharmaceutical solution consisting of hydromorphone and/or a pharmaceutically acceptable salt(s) thereof (e.g., hydromorphone hydrochloride) and water.

A further aspect of the disclosure provides a method for manufacturing a pharmaceutical solution, the method comprising (i) combining hydromorphone, a pharmaceutically acceptable salt(s) thereof, or combinations thereof with sterile water in the absence of buffers and/or other additives, and (ii) dissolving the hydromorphone and/or the pharmaceutically acceptable salt(s) thereof to form the solution. In one particular embodiment, the pharmaceutically acceptable salt is hydromorphone hydrochloride. In this or other embodiments, the method may further comprise (iii) sparging the sterile water with an inert gas prior to combining with the hydromorphone and/or the pharmaceutically acceptable salt(s) thereof, and/or (iv) sparging the resulting solution after the hydromorphone, and/or the pharmaceutically acceptable salt(s) thereof, is dissolved in the sterile water.

Yet another aspect of the present disclosure is a method of treating pain in a subject, the method comprising administering intrathecally a sterile, pharmaceutical solution comprising hydromorphone, a pharmaceutically acceptable salt(s) thereof, or combinations thereof, wherein the solution is substantially free of buffer and optionally one or more other additives.

Other aspects of the disclosure are described in more detail below.

DETAILED DESCRIPTION OF THE DISCLOSURE

Figure 1:
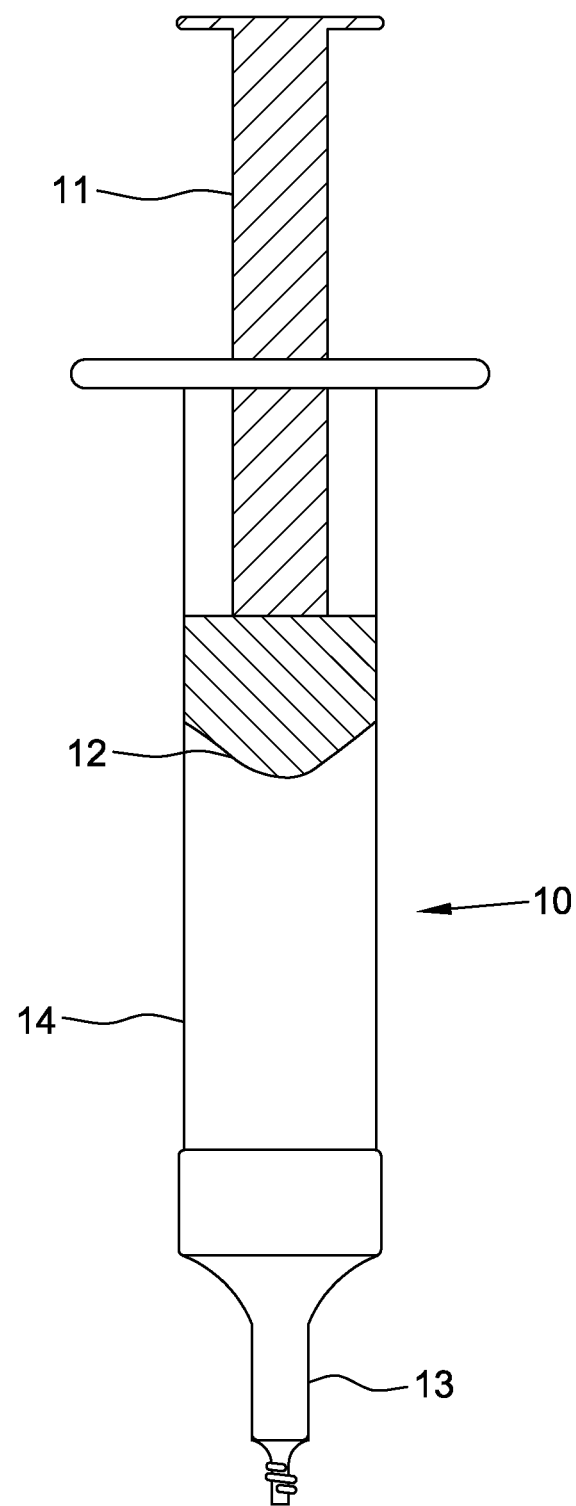
FIG. 1 is an illustration of a syringe containing a hydromorphone solution according to an exemplary embodiment.

The present disclosure provides sterile solutions of hydromorphone, and/or one or more pharmaceutically acceptable salts thereof, that are suitable for intrathecal injection. Advantageously, the hydromorphone solutions of the present disclosure are substantially free of buffer and optionally one or more other additives, yet have a pH closer to the physiological pH of cerebrospinal fluid than formulations containing buffer. Also disclosed are methods for the manufacture of such hydromorphone solutions, as well as methods for the use thereof.

Overview

The present disclosure is based on the finding that hydromorphone and/or one or more pharmaceutically acceptable salts thereof can be formulated as an intrathecal solution, without the need for buffers or other additives to maintain stability of the solution and/or pH of the solution within a desired range.

As demonstrated in the examples, hydromorphone solutions formulated without buffers or other additives have a pH higher than that of hydromorphone solutions containing buffer, and exhibit little if any change (e.g., decrease) in pH over extended periods of storage. Since intrathecal delivery of hydromorphone and its salts is via direct injection into the CSF, and it is desirable to keep the pH of the resulting CSF—hydromorphone solution mixture as close to the physiological pH of the CSF (i.e., about 7.3) as possible, injection of a hydromorphone solution with a pH near 7.3 is appealing. The hydromorphone solutions of the present disclosure, which have a pH closer to the natural physiological pH of CSF than a hydromorphone solution containing buffer, thus provide an unexpected advantage over hydromorphone solutions containing buffers.

Additionally, since hydromorphone solutions of the present disclosure are intended for intrathecal administration, it is also desirable for the pH of the solutions to be sufficiently high to prevent corrosion of delivery pumps used during intrathecal administration. Accordingly, the solutions of the present disclosure have a pH above about 3, and more particularly have a pH from about 3 to about 7, or from about 3.5 to about 7. For instance, some embodiments may have a pH from about 3.5 to about 5.5, or from about 3.7 to about 5.3, or from about 3.9 to about 5.1, or from about 4.2 to about 5, while other embodiments may have a pH from about 3 to about 5, or from about 4 to about 5, or from about 4.5 to about 5. Advantageously, buffers are not needed to maintain the pH of the hydromorphone solutions of the present disclosure within this range, even over extended periods of storage.

As further demonstrated in the examples, solutions of the present disclosure also advantageously maintain their stability, and have low levels of impurities (also referred to herein as "side products"), over extended periods of storage. Buffer or other stability-enhancing additives are thus not necessary to maintain stability of the hydromorphone solutions.

Because hydromorphone solutions of the present disclosure are substantially free of buffer and optionally one or more other additives, the risk of potential complications, such as toxicity or other side effects, allergic responses and/or granuloma formation, is lowered in comparison to hydromorphone compositions comprising buffer and/or other additives. Further, the use of less or no buffer or other additives decreases the costs of producing the hydromorphone solutions, and thus reduces manufacturing complexity.

Hydromorphone Solutions

The present disclosure provides sterile solutions of hydromorphone and/or a pharmaceutically acceptable salt(s) thereof. The drug hydromorphone, as depicted above, is comprised of 4,5-α-epoxy-3-hydroxy-17-methyl morphinan-6-one, and possesses analgesic properties. As used herein, the term "hydromorphone solution" is intended to encompass solutions containing hydromorphone, one or more pharmaceutically acceptable salts of hydromorphone, or combinations thereof. Suitable hydromorphone salts include any water soluble salt of hydromorphone, including those selected from the group consisting of a hydromorphone sulfate, hydromorphone hydrochloride, hydromorphone sodium chloride, hydromorphone trifluoracetate, hydromorphone thiosemicarbazone hydrochloride, hydromorphone pentafluoropropionate, hydromorphone p-nitrophenyl-hydrozone, hydromorphone hydrazine, hydromorphone hydrobromide, hydromorphone mucate, hydromorphone methylbromide, hydromorphone oleate, hydromorphone n-oxide, hydromorphone acetate, hydromorphone phosphate dibasic, hydromorphone phosphate monobasic, hydromorphone inorganic salt, hydromorphone organic salt, hydromorphone acetate trihydrate, hydromorphone bis(heptafluorobutyrate), hydromorphone bis(methylcarbamate), hydromorphone (bis-pentafluoropropionate), hydromorphone bis(pyridine-3-carboxylate), hydromorphone bis(trifluoroacetate), hydromorphone bitartrate, hydromorphone chlorohydrate, and hydromorphone sulfate pentahydrate. Preferably, the hydromorphone solutions of the present disclosure comprise hydromorphone hydrochloride.

In one embodiment, the solution of the present disclosure comprises, consists essentially of, or consists of hydromorphone and/or one or more pharmaceutically acceptable salt(s) of hydromorphone, and sterile water, wherein the pharmaceutically acceptable salt(s) is other than hydromorphone hydrochloride. For instance, in one embodiment, the solution comprises, consists essentially of, or consists of hydromorphone and/or one or more pharmaceutically acceptable salt(s) of hydromorphone, and water, wherein the pharmaceutically acceptable salt(s) is selected from the group consisting of a hydromorphone sulfate, hydromorphone sodium chloride, hydromorphone trifluoracetate, hydromorphone thiosemicarbazone hydrochloride, hydromorphone pentafluoropropionate, hydromorphone p-nitrophenyl-hydrozone, hydromorphone hydrazine, hydromorphone hydrobromide, hydromorphone mucate, hydromorphone methylbromide, hydromorphone oleate, hydromorphone n-oxide, hydromorphone acetate, hydromorphone phosphate dibasic, hydromorphone phosphate monobasic, hydromorphone inorganic salt, hydromorphone organic salt, hydromorphone acetate trihydrate, hydromorphone bis(heptafluorobutyrate), hydromorphone bis(methylcarbamate), hydromorphone (bis-pentafluoropropionate), hydromorphone bis(pyridine-3-carboxylate), hydromorphone bis(trifluoroacetate), hydromorphone bitartrate, hydromorphone chlorohydrate, hydromorphone sulfate pentahydrate, and combinations thereof.

Solutions of the present disclosure may include hydromorphone and/or one or more pharmaceutically acceptable salts thereof, wherein the total concentration of hydromorphone and/or pharmaceutically acceptable salt(s) thereof is about 1 mg/ml or more, including, for example, about 1 mg/ml, about 2 mg/ml, about 5 mg/ml, about 10 mg/ml, about 15 mg/ml, about 20 mg/ml, or about 25 mg/ml. Typically, the hydromorphone solutions comprise hydromorphone and/or one or more pharmaceutically acceptable salts thereof in a total concentration (i.e., concentration of any hydromorphone and pharmaceutically acceptable salt(s) thereof in the solution) of from about 1 mg/ml to about 25 mg/ml, or from about 2 mg/ml to about 25 mg/ml, or from about 2 mg/ml to about 20 mg/ml, or from about 2 mg/ml to about 15 mg/ml, or from about 2 mg/ml to about 10 mg/ml, or from about 2 mg/ml to about 5 mg/ml, or from about 5 mg/ml to about 25 mg/ml, or from about 5 mg/ml to about 20 mg/ml, or from about 5 mg/ml to about 15 mg/ml, or from about 5 mg/ml to about 10 mg/ml, or from about 10 mg/ml to about 15 mg/ml. In some particular embodiments, the total concentration of hydromorphone and pharmaceutically acceptable salt(s) thereof is about 2 mg/ml, about 5 mg/ml, about 10 mg/ml, or about 15 mg/ml, with a concentration of about 10 mg/ml being preferred.

Hydromorphone solutions of the present disclosure are aqueous solutions, i.e., the hydromorphone and/or pharmaceutically acceptable salt(s) thereof is dissolved in water, and preferably, sterile water for injection (WFI). As used herein, the term "water" or "sterile water" does not encompass bacteriostatic water (i.e., water comprising benzyl alcohol as a bacteriostatic preservative). Indeed, in some embodiments, nothing other than the hydromorphone and/or pharmaceutically acceptable salt(s) thereof and water is used to form the resulting hydromorphone solution.

The hydromorphone and/or pharmaceutically acceptable salt(s) thereof and water included in solutions of the present disclosure preferably meet USP standards for quality (e.g., USP <1>, injections).

Hydromorphone solutions of the present disclosure may have a viscosity similar to that of water at room temperature (e.g., about 20° C.). For instance, a given solution may have a viscosity of about 2 centipoise (cps) or less (e.g., a viscosity of about 1 cps) at room temperature.

As previously noted, in view of various considerations (e.g., pump corrosion, pH of CSF, etc.), hydromorphone solutions of the present disclosure have a pH of at least about 3. Typically, the pH of the solution is from about 3 to about 7, or from about 3.5 to about 7, or from about 3 to about 5.5, or from about 3.5 to about 5.5, or from about 3.7 to about 5.3, or from about 3.9 to about 5.1, or from about 4.2 to about 5, or from about 3 to about 5, or from about 4 to about 5, or from about 4.5 to about 5.

It has been discovered that the hydromorphone solutions of the present disclosure only exhibit little if any change in pH (e.g., a small decrease in pH), even over extended periods of storage. For example, the pH of the solutions will typically remain within the range of from about 3 to about 7, and or within the range of from about 3.5 to about 5.5, or from about 3.7 to about 5.3, or from about 3.9 to about 5.1, or from about 4 to about 5, or from about 4.5 to about 5, for at least about 1 month, at least about 2 months, at least about 3 months, at least about 6 months, at least about 1 year, or at least about 2 years. Preferably, the pH of the solutions will remain within these ranges when stored at about 25° C. and about 60% relative humidity (RH), about 30° C. and about 65% RH, or about 40° C. and about 75% RH over these time periods. In some exemplary embodiments, the hydromorphone solutions have a pH of at least about 3, and more preferably at least about 4 or at least about 4.5, when stored for at least about 1 month, and preferably for at least about 2 months, at least about 3 months, at least about 6 months, at least about 1 year, or at least about 2 years at about 25° C. and about 60% RH, about 30° C. and about 65% RH, or about 40° C. and about 75% RH. In some embodiments, the hydromorphone solutions have a pH of at least about 4.5 when stored for about 3 months at (i) about 25° C. and about 60% RH, (ii) about 30° C. and about 65% RH, or (iii) about 40° C. and about 75% RH.

Buffers and Other Additives

The hydromorphone solutions of the present disclosure are substantially free of buffers and optionally one or more other additives, as further described and detailed herein below.

It has now been discovered that buffers and other additives are not needed to maintain the pH and/or stability of the hydromorphone solutions of the present disclosure. As inclusion of buffers and other additives to a composition can lead to potential complications, such as toxicity or other side effects, allergic responses and/or granuloma formation, the hydromorphone solutions of the present disclosure have an unexpected advantage over hydromorphone solutions containing such additives. Further, the exclusion of buffer or other additives from the solutions would decrease the costs of producing the hydromorphone solutions, and reduce manufacturing complexity.

As used herein, "buffer" refers to a substance used to resist change in pH over time or upon dilution or addition of acid or alkali. A buffer may be, for example, an ionic compound (e.g., a salt or weak acid or base) that is added to a solution to resist changes in its acidity or alkalinity, and thus stabilize the pH of the solution. A "buffer" may also refer to an agent which aids in maintaining stability of a compound in solution. Buffers may include, by way of example and without limitation, phosphates such as potassium metaphosphate, potassium phosphate; acetates, such as monobasic sodium acetate; citrates, such as sodium citrate, sodium citrate anhydrous and dehydrate, and citric acid; salts of inorganic or organic acids; salts of inorganic or organic bases; and others known to those of ordinary skill in the art. The solutions of the present disclosure are substantially free of buffer, and preferably are completely free of buffer.

As used herein, "other additives" generally refers to and includes any other additives, components or agents that may be added to the solutions of the present disclosure, including those that have been known to be included in pharmaceutical compositions or solutions—such as hydromorphone solutions. Additives that may optionally be excluded from, or not added to, the solutions of the disclosure may include, without limitation: an active pharmaceutical ingredient ("API") other than hydromorphone or pharmaceutically acceptable salts of hydromorphone; acids; pH adjusters; preservatives; polymeric materials; emulsifiers; lubricants; antioxidants; suspending agents; excipients (other than water); diluents; oils; surfactants; saline; solvents; metal salts; minerals; vitamins; sterilizers; and stabilizers. The solutions of the present disclosure are optionally substantially free of one or more of such additives, or may be completely free of one or more of such additives. In certain embodiments, the solutions are substantially free of all such additives, or may be completely free of all such additives.

Thus, in one aspect, hydromorphone solutions of the disclosure are substantially free (or completely free) of buffer and are also substantially free (or completely free) of one or more of the following other additives: an API other than hydromorphone or pharmaceutically acceptable salts of hydromorphone; acids; pH adjusters; preservatives; polymeric materials; emulsifiers; lubricants; antioxidants; suspending agents; excipients (other than water); diluents; oils; surfactants; saline; solvents; metal salts; minerals; vitamins; sterilizers; stabilizers, or any combination of these additives.

The API which may be excluded from, or not added to, the solutions of the disclosure may include opioids and salts, prodrugs, esters, derivatives, or analogs thereof (other than hydromorphone and its pharmaceutically acceptable salts). In general, opioids and opioid derivatives are active in binding to the opioid receptor and may include an opioid receptor agonist or antagonist, and may include both natural and synthetic compounds. Examples of opioids or opioid derivatives include, but are not limited to, morphine (and structurally related analogs and derivatives), alvimopan, benzomorphans, buprenorphine, codeine, 6-desomorphine, dihydromorphine, dihydromorphinone, dihydrocodeine, dihydrocodeinone, 3,6-diacetylmorphine, 6-methylene-dihydromorphine, diphenoxylate, drotebanol, eseroline, etorphine, etonitazine, fentanyl, fentanyl congeners (e.g., sufentanil, alfentanil, lofentanil, carfentanil, remifentanil, trefentanil, and mirfentanil), hydrocodone, levophenacylmorphan, methadone, oxymorphone, α-oxymorphamine, nicomorphine, pethidine, picenadol, tapentadole, thebaine, trimebutane, asimadoline, butorphanol, bremazocine, cyclazocine, dextromethorphan, dynorphin, enadoline, ketazocine, nalbuphine, nalfurafine, norbuprenorphine, oxycodone, pentazocine, salvinorin A, 2-methoxymethyl salvinorin B and its ethoxymethyl and fluoroethoxymethyl homologues, spiradoline, tifluadom, deltorphin, ethoxymetopon, leu-enkephalin, met-enkephalin, mitragyna speciosa (kratom), mitragynine, mitragynine-pseudoindoxyl, N-phenethyl-14-norbuprenorphine, norclozapine, 7-spiroindanyloxymorphone, naloxone, and the like.

The API which may be excluded from, or not added to, the solutions of the disclosure may also include other analgesics or anesthetics, such as bupivacaine, lidocaine, clonidine, baclofen, fentanyl citrate, sufentanil citrate, flupiritine, ketamine, acetaminophen, ibuprofen, fluriprofen, ketoprofen, voltaren, phenacetin, salicylamide, or pharmaceutically acceptable salts thereof.

The API which may be excluded from, or not added to, the solutions of the disclosure may also include omega-conopeptides; antibodies; glycoproteins; doxapram or salts thereof; anti-inflammatories (e.g., naproxen and indomethacin); antihistamines (e.g., chlorpheniramine maleate, phenindamine tartrate, pyrilamine maleate, doxylamine succinate, phenyltoloxamine citrate, diphenhydramine hydrochloride, promethazine, brompheniramine maleate, dexbrompheniramine maleate, clemastine fumarate and triprolidine); antitussives; expectorants; decongestants; antibiotics (e.g., amebicides, broad and medium spectrum, final medications, monobactams and viral agents, such as erythromycin, penicillin and cephalosporins and their derivatives); bronchodilators; cardiovascular preparations; central nervous system drugs; immunomodulators; immunosuppressives; thyroid preparations; steroids and hormones (e.g., norepinephrine; ACTH, anabolics, androgen and estrogen combinations, androgens, corticoids and analgesics, estrogens, glucocorticoid, gonadotropin, gonadotropin releasing, human growth hormone, hypocalcemic, menotropins, parathyroid, progesterone, progestogen, progestogen and estrogen combinations, somatostatin-like compounds, urofollitropin, vasopressin, and others); and the like.

The "other additives" which may be excluded from, or not added to, hydromorphone solutions of the disclosure may be an acid. Acids include carboxylic acid and salts thereof. The term "carboxylic acid" refers to any suitable carboxylic acid, usually a monocarboxylic acid, dicarboxylic acid, or tricarboxylic acid, more usually a monocarboxylic acid or dicarboxylic acid, normally a monocarboxylic acid. The carboxylic acid may be a "low molecular weight carboxylic acid", i.e., a carboxylic acid having less than 8 carbon atoms. Examples of carboxylic acids include acetic acid, lactic acid and salts thereof.

The "other additives" which may be excluded from, or not added to, hydromorphone solutions of the disclosure may be a pH adjuster. As used herein, "pH adjuster" refers to a substance used to increase or decrease pH upon addition to a composition. Such adjusters include, for example, acids or alkali. Specific examples include, but are not limited to, hydrochloric acid solutions, sodium hydroxide, sulfates, etc.

The "other additives" which may be excluded from, or not added to, hydromorphone solutions of the disclosure may be a preservative. Preservatives are well known, and generally include compounds for inhibiting or preventing microbial activity, including growth. Non-limiting examples of preservatives include mercury-containing substances such as merfen and thiomersal; stabilized chlorine dioxide; and quaternary ammonium compounds such as benzalkonium chloride, cetyltrimethylammonium bromide and cetylpyridinium chloride; and the like. Other examples of preservatives include benzethonium chloride, benzyl alcohol, chlorobutanol, phenol, phenylethyl alcohol, phenylmercuric nitrate, thimerosal, and others known to those of ordinary skill in the art.

The "other additives" which may be excluded from, or not added to, hydromorphone solutions of the disclosure may be a polymeric material. Non-limiting examples of polymeric materials include polysulfated glucosoglycans, glucosaminoglycans, mucopolysaccharides (e.g., chondroitins, such as chondroitin sulfate; and hyaluronic acid and its salts such as sodium hyaluronate), cellulose derivatives (e.g., carboxymethylcellulose sodium, hydroxyethyl cellulose, hydroxypropyl cellulose, etc.), and derivatives thereof and mixtures thereof. The term "polymeric material" includes individual polymeric materials, such as those listed above, combinations of two or more different polymeric materials, and polymeric matrices, such as described in WO 97/11681.

The "other additives" which may be excluded from, or not added to, hydromorphone solutions of the disclosure may be a lubricant. Lubricants include, but are not limited to fatty esters, glyceryl monooleate, glyceryl monostearate, wax, carnauba wax, beeswax, vitamin E succinate, and the like, and combinations thereof.

The "other additives" which may be excluded from, or not added to, hydromorphone solutions of the disclosure may be an antioxidant. The term "antioxidant" refers to an agent that inhibits oxidation and thus is used to prevent the deterioration of compositions by oxidation due to the presence of oxygen free radicals or free metals in the composition. Such compounds include, by way of example and without limitation, ascorbic acid (Vitamin C), ascorbyl palmitate, butylated hydroxyanisole (BHA), butylated hydroxytoluene (BHT), hypophosphorous acid, monothioglycerol, sodium ascorbate, sodium formaldehyde sulfoxylate, sodium metabisulfite, sodium bisulfate, vitamin E and its derivatives, propyl gallate and others known to those of ordinary skill in the art.

The "other additives" which may be excluded from, or not added to, hydromorphone solutions of the disclosure may be a surfactant. Surfactants include soaps, synthetic detergents, and wetting agents. Surfactants may be cationic surfactants, anionic surfactants, non-ionic surfactants, or amphoteric surfactants. Examples of surfactants include Polysorbate 80; sorbitan monooleate; sodium lauryl sulfate (sodium dodecylsulfate); soaps such as fatty acid alkali metal salts, ammonium salts, and triethanolamine salts; cationic detergents such as dimethyl dialkyl ammonium halides, alkyl pyridinium halides, and alkylamine acetates; anionic detergents such as alkyl, aryl and olefin sulfonates, alkyl, olefin, ether and monoglyceride sulfates, and sulfosuccinates; non-ionic detergents such as fatty amine oxides, fatty acid alkanolamides, and poly(oxyethylene)-block-poly(oxypropylene) copolymers; and amphoteric detergents, for example, alkyl β-aminopropionates and 2-alkylimidazoline quaternary ammonium salts; wetting agents such as, glycerin, proteins, and peptides; water miscible solvents such as glycols; and mixtures thereof. Examples of surfactants also include phospholipids (e.g., egg-yolk lecithin or soybean lecithin, phosphatidylinocytol, phosphatidyl ethanolamine, phosphatidylserine, sphingomyelene, phosphatidylcholine), polyethylene glycol, polyoxyalkylene copolymer, and sorbitan fatty acid ester.

The "other additives" which may be excluded from, or not added to, hydromorphone solutions of the disclosure may be an oil. Non-limiting examples of oils include simple lipids, derived lipids, complex lipids that are derived from natural vegetable oil and fat, animal oil and fat, and mineral oil, or a mixture of those. The oil may be soybean oil, olive oil, sesame oil, castor oil, corn oil, peanut oil, safflower oil, grape seed oil, eucalyptus oil, medium-chain fatty acid ester, or low-chain fatty acid ester. Animal oils and fat include, but are not limited to, cod-liver oil, seal oil, sardine oil, docosahexiaenoic acid, and eicosapentaenoic acid. Mineral oils include, but are not limited to, liquid paraffins.

The "other additives" which may be excluded from, or not added to, hydromorphone solutions of the disclosure may be a stabilizer. Stabilizers include substances that act to prevent oxidation, for example, by controlling or trapping those substances (e.g., metals) that may cause oxidation. Examples of stabilizers include metal-sequestering agents, such as ethylenediamine tetraacetic acid (EDTA).

The "other additives" which may be excluded from, or not added to, hydromorphone solutions of the disclosure may be a metal salt (e.g. potassium chloride, sodium chloride, and lithium carbonate); mineral (e.g., iron, chromium, molybdenum and potassium); or vitamin (e.g., water-soluble vitamins such as B complex, vitamin C, vitamin B12 and folic acid and veterinary formulations); sterilizer (e.g., benzyl alcohol); and the like. In one embodiment, the hydromorphone solutions of the present disclosure are substantially free of sodium chloride.

The "other additives" which may be excluded from, or not added to, hydromorphone solutions of the disclosure may be an emulsifier, excipient, diluent, solvent, or suspending agent. Emulsifiers, excipients, diluents, solvents, and suspending agents are well known to those skilled in the art. Specific examples include bacteriostatic water, but not water or sterile water, as defined herein.

Sterilization and Stability

The hydromorphone solutions of the present disclosure are advantageously sterile and suitable for intrathecal injection. While there are no absolute FDA standards for sterilization processes, pharmaceutical solutions are most commonly sterilized using a heating regimen at about 121° C. with an $F_o$ of about 30 minutes. While this may be an effective method for thermally stable compounds, this practice is counterproductive for some heat-labile active pharmaceutical ingredients (API's). In these cases, the resulting solution may be sterile, but it is often plagued with an unacceptable increase in degradation products brought on by the excessive use of heat in the sterilization process. Furthermore, compositions containing heat-labile API's are often not terminally sterilized to avoid this degradation. Therefore, it is desirable to find and implement a sterilization method that utilizes less harsh conditions in order to prevent this thermal degradation from taking place, while continuing to meet sterility standards.

Indeed, during the terminal sterilization process, heat-labile hydromorphone undergoes transformations to undesirable side products such as hydromorphone N-oxide (HNO), 6-β-tetrahydroooripavine (THO), dihydromorphine (DHM), and pseudo-hydromorphone (PHM). This obviously reduces the amount of hydromorphone in solution, and thus the overall efficacy of the solution. Additionally, the degradation products may have undesirable side effects, including toxicity. The amount of side products found in commercially available non-terminally sterilized hydromorphone solutions is shown in the table below.

| Hydromorphone Hydrochloride (Commercial) 10 mg/mL | | | |
|---|---|---|---|
| % HNO | % THO | % DHM | % PHM |
| <0.05 | <0.05 | <0.05 | 0.5 |

An alternative to terminal sterilization is aseptic processing, which is the process by which a sterile (aseptic) product is packaged in a sterile container in a way which maintains sterility. This avoids the harsh conditions of terminal sterilization without sacrificing sterility of the resulting solution. It was hypothesized that aseptic processing may lead to a solution with fewer degradation products, as the hydromorphone would not be subjected to the rigors of the terminal sterilization process.

Therefore, there is a clinical need for aqueous solutions of hydromorphone having fewer degradation products, preferably for concentrated solutions that are also stable in a variety of storage conditions for extended periods of time. Due to the heat-lability of the hydromorphone product, aseptic processing is herein disclosed for the reduction of impurities in the hydromorphone solution.

In some embodiments, the aseptic processing may involve filtering the hydromorphone solutions prior to aseptic filling of a container (e.g., vial, ampule, or syringe) with the hydromorphone solution, as described herein.

In addition to being sterile, the hydromorphone solutions of the present disclosure also maintain their stability and have low levels of impurities after extended periods of storage and under varying storage conditions. The stability (as measured by % label claim) and level of impurities present in the solutions can be determined using high performance liquid chromatography (HPLC), as discussed in the examples, and in particular Example 8.

The hydromorphone solutions of the present disclosure are preferably stable after storage for at least about 1 month, at least about 2 months, at least about 3 months, at least about 6 months, at least about 1 year, or at least about 2 years of storage. Preferably, the hydromorphone solutions of the present disclosure are stable after storage for at least about 1 month, at least about 2 months, at least about 3 months, at least about 6 months, at least about 1 year, or at least about 2 years of storage at a temperature of at least about 25° C., at least about 30° C., or at least about 40° C. In some particular embodiments, the hydromorphone solutions of the present disclosure are stable after storage for at least about 1 month, at least about 2 months, at least about 3 months, at least about 6 months, at least about 1 year, or at least about 2 years of storage at about 25° C. and about 60% RH, at about 30° C. and about 65% RH, or at about 40° C. and about 75% RH.

The hydromorphone solutions also preferably contain low levels of impurities. Impurities may include, for example, pseudo-hydromorphone, dihydromorphone, hydromorphone N-oxide, 6-β-tetrahydrooripavine, morphine, 8,14-dihydrooripavine, and unknown impurities. Impurity levels may be measured using any technique known to those skilled in the art, and preferably are determined using HPLC, such as discussed in Example 8.

Preferably, the hydromorphone solutions of the present disclosure contain less than about 1%, or less than about 0.5%, or less than about 0.15%, or less than about 0.05% of pseudo-hydromorphone, as a percent of the active peak (% area) as determined using HPLC. Preferably, the solutions are substantially free of pseudo-hydromorphone, and more preferably are free of detectable levels of pseudo-hydromorphone.

Preferably, the hydromorphone solutions of the present disclosure contain less than about 0.2%, or less than about 0.1%, or less than about 0.05% of hydromorphone N-oxide, as a percent of the active peak (% area) as determined using HPLC. Preferably, the solutions are substantially free of hydromorphone N-oxide, and more preferably are free of detectable levels of hydromorphone N-oxide.

Preferably, the hydromorphone solutions of the present disclosure contain less than about 0.2%, or less than about 0.15%, or less than about 0.05% of dihydromorphone, as a percent of the active peak (% area) as determined using HPLC. Preferably, the solutions are substantially free of dihydromorphone, and more preferably are free of detectable levels of dihydromorphone.

Preferably, the hydromorphone solutions of the present disclosure contain less than about 0.2%, or less than about 0.1%, or less than about 0.05% of 6-β-tetrahydrooripavine, as a percent of the active peak (% area) as determined using HPLC. Preferably, the solutions are substantially free of 6-β-tetrahydrooripavine, and more preferably are free of detectable levels of 6-β-tetrahydrooripavine.

Preferably, the hydromorphone solutions of the present disclosure contain less than about 0.2% of morphine, more preferably contain less than about 0.15%, or less than about 0.05% of morphine, as a percent of the active peak (% area) as determined using HPLC. Preferably, the solutions are free of morphine.

Preferably, the hydromorphone solutions of the present disclosure contain less than about 0.2% of 8,14-dihydrooripavine, and more preferably contain less than about 0.1%, or less than about 0.05% of 8,14-dihydrooripavine, as a percent of the active peak (% area) as determined using HPLC. Preferably, the solutions are substantially free of 8,14-dihydrooripavine, and more preferably are free of detectable levels of 8,14-dihydrooripavine.

Preferably, the hydromorphone solutions of the present disclosure contain less than about 0.2%, or less than about 0.1%, or less than about 0.05% of unknown impurities, as a percent of the active peak (% area) as determined using HPLC. Preferably, the solutions are substantially free of unknown impurities, and more preferably are free of detectable levels unknown impurities.

Preferably, the hydromorphone solutions of the present disclosure contain less than about 1% of total impurities, more preferably contain less than about 0.5%, or less than about 0.2%, or less than about 0.1%, or less than about 0.05% of total impurities, as a percent of the active peak (% area) as determined using HPLC. Preferably, the solution is substantially free of impurities, and more preferably are free of detectable levels of impurities. The level of total impurities includes the amounts of known impurities, such as pseudo-hydromorphone, hydromorphone N-oxide, dihydromorphone, 6-β-tetrahydrooripavine, morphine, and 8,14-dihydrooripavine, as well as the amounts of unknown impurities.

In preferred embodiments, the hydromorphone solutions of the present disclosure are stable and contain less than about 1% of pseudo-hydromorphone, less than about 0.2% of hydromorphone N-oxide, less than about 0.2% of dihydromorphone, less than about 0.2% of 6-β-tetrahydrooripavine, less than about 0.2% of unknown impurities, less than about 1% of total impurities, as a percent of the active peak (% area) as determined using HPLC, or any combination thereof. In other preferred embodiments, the hydromorphone solutions of the present disclosure are stable and contain less than about 1% or less than about 0.15% of pseudo-hydromorphone, less than about 0.05% of hydromorphone N-oxide, less than about 0.05% of dihydromorphone, less than about 0.05% of 6-β-tetrahydrooripavine, as a percent of the active peak (% area) as determined using HPLC, or any combination thereof. In other embodiments, the hydromorphone solutions are stable and are substantially free of pseudo-hydromorphone, hydromorphone N-oxide, dihydromorphone, 6-β-tetrahydrooripavine, or any combination thereof.

Preferably, the hydromorphone solutions will meet one or more of the above-listed impurity levels after storage at about 25° C. and about 60% RH, at about 30° C. and about 65% RH, or at about 40° C. and about 75% RH for at least 1 month, at least about 2 months, at least about 3 months, at least about 6 months, at least about 1 year, or at least about 2 years.

The hydromorphone solutions of the present disclosure also have low levels of particulates. Particulates may include undissolved hydromorphone or pharmaceutically acceptable salts thereof, or other particulate matter. The amount of particulates present in the hydromorphone solutions may be determined using any suitable method known to those skilled in the art including, for example, the Light Obscuration Particle Count Test described in USP 788. The hydromorphone solutions preferably meet the USP limits for particulate levels for 10 μm or greater and 25 μm or greater sized particulates, which is 6000 and 600, respectively. Preferably, the hydromorphone solutions will meet these limits after storage at about 25° C. and about 60% RH, at about 30° C. and about 65% RH, or at about 40° C. and about 75% RH for at least about 1 month, at least about 2 months, at least about 3 months, at least about 6 months, at least about 1 year, or at least about 2 years.

In some embodiments, the hydromorphone solutions may contain about 1300 or less, about 1000 or less, about 750 or less, about 600 or less, about 400 or less or about 200 or less of 10 nm or greater sized particulates, and/or may comprise about 40 or less, about 20 or less, or about 10 or less of 25 μm or greater sized particulates, or combinations thereof. Preferably, the hydromorphone solutions are free of particulates, and in particular, are free of undissolved hydromorphone or pharmaceutically acceptable salt.

In an embodiment, a solution of intrathecal hydromorphone hydrochloride contains less than 1.0% pseudo-hydromorphone.

According to a further embodiment, a solution of intrathecal hydromorphone hydrochloride contains less than 0.1% pseudo-hydromorphone.

In an embodiment, a solution of intrathecal hydromorphone hydrochloride contains less than 0.2% hydromorphone N-oxide.

According to another embodiment, a solution of intrathecal hydromorphone hydrochloride is substantially free of hydromorphone N-oxide.

According to another embodiment, a solution of intrathecal hydromorphone hydrochloride is substantially free of dihydromorphone.

According to another embodiment, a solution of intrathecal hydromorphone hydrochloride is substantially free of 6-β-tetrahydrooripavine.

According to one embodiment, the solution described herein is not terminally sterilized.

According to another embodiment, the solution described herein is free, or substantially free, of particulates.

According to yet another embodiment, the solution described herein is stable at 25° C. and 60% relative humidity for at least 1 month.

According to yet another embodiment, the solution described herein is stable at 30° C. and 65% relative humidity for at least 1 month.

According to a further embodiment, the solution described herein is stable at 40° C. and 75% relative humidity for at least 1 month.

According to yet another embodiment, the solution described herein is stable at 25° C. and 60% relative humidity for at least 3 months.

According to yet another embodiment, the solution described herein is stable at 30° C. and 65% relative humidity for at least 3 months.

According to a further embodiment, the solution described herein is stable at 40° C. and 75% relative humidity for at least 3 months.

According to yet another embodiment, the solution described herein is stable at 25° C. and 60% relative humidity for at least 6 months.

According to yet another embodiment, the solution described herein is stable at 30° C. and 65% relative humidity for at least 6 months.

According to a further embodiment, the solution described herein is stable at 40° C. and 75% relative humidity for at least 6 months.

According to yet another embodiment, the solution described herein is stable at 25° C. and 60% relative humidity for at least 1 year.

According to yet another embodiment, the solution described herein is stable at 30° C. and 65% relative humidity for at least 1 year.

According to a further embodiment, the solution described herein is stable at 40° C. and 75% relative humidity for at least 1 year.

According to yet another embodiment, the solution described herein is stable at 25° C. and 60% relative humidity for at least 2 years.

According to yet another embodiment, the solution described herein is stable at 30° C. and 65% relative humidity for at least 2 years.

According to a further embodiment, the solution described herein is stable at 40° C. and 75% relative humidity for at least 2 years.

Disclosed herein is a pharmaceutical solution comprising a sterile, intrathecal, aqueous hydromorphone hydrochloride solution, wherein said composition is substantially free of buffer.

According to another embodiment, the solution described herein is suitable for intrathecal delivery.

Disclosed herein is a pharmaceutical composition consisting of a sterile, aqueous solution of hydromorphone hydrochloride.

In an embodiment, the concentration of the hydromorphone hydrochloride solution is 10.0 mg/mL.

In an embodiment, the concentration of the hydromorphone hydrochloride solution is 2.0 mg/mL.

Disclosed herein in an embodiment is a sterile pharmaceutical solution comprising hydromorphone and/or a pharmaceutically acceptable salt(s) thereof, wherein the solution is substantially free of buffer and optionally one or more other additives. In one particular embodiment, the solution comprises hydromorphone hydrochloride.

In some embodiments, the hydromorphone compositions consist essentially of hydromorphone and/or one or more pharmaceutically acceptable salts thereof and water. Thus, also provided is a sterile pharmaceutical solution consisting essentially of hydromorphone and/or one or more pharmaceutically acceptable salts thereof and water. In such an embodiment, the solution may contain impurities inherently formed as a result of degradation of the hydromorphone or salt thereof, but does not contain impurities, buffers, or other substances or additives that have been affirmatively added to or included in the composition. In one particular embodiment, the pharmaceutically acceptable salt is hydromorphone hydrochloride.

Also disclosed herein in an embodiment is a sterile pharmaceutical solution comprising hydromorphone and/or one or more pharmaceutically acceptable salts thereof, wherein the solution is substantially free (or completely free) of buffer and also substantially free (or completely free) of one or more (e.g., any combination) of the following: API other than hydromorphone or pharmaceutically acceptable salt(s) of hydromorphone; acids; pH adjusters; preservatives; polymeric materials; emulsifiers; lubricants; antioxidants; suspending agents; excipients (other than water); diluents; oils; surfactants; saline; solvents; metal salts; minerals; vitamins; sterilizers; and stabilizers.

Method of Manufacture and Storage

Also provided are methods for manufacturing hydromorphone solutions disclosed herein. The solutions may be prepared by combining the desired amount of hydromorphone and/or pharmaceutically acceptable salt(s) thereof with sterile water, in the absence of buffers and optionally one or more other additives, and dissolving the hydromorphone and/or pharmaceutically acceptable salt(s) thereof to form a hydromorphone solution of the present disclosure. This dissolving of the hydromorphone and/or pharmaceutically acceptable salt(s) thereof may occur simply as a result of the combining or may be facilitated by mixing or stirring the hydromorphone and/or pharmaceutically acceptable salt(s) thereof and water using any suitable technique. Upon completion of the dissolving, the solution is preferably homogenous, and there is little or no undissolved hydromorphone or pharmaceutically acceptable salts thereof detected (using methods generally known in the art) or present in the solution. Optionally, additional sterile water, and/or hydromorphone and/or pharmaceutically acceptable salt(s) thereof, may be added and dissolved into the solution as desired, in order to alter the concentration of the hydromorphone and/or pharmaceutically acceptable salt(s) thereof in the final solution to the desired level.

It has been discovered that oxygen, including oxygen inherently present in the water (i.e., dissolved in the water) used to prepare the hydromorphone solutions, may impact the stability and pH of the final solution. More particularly, oxygen may increase the degree of degradation of the hydromorphone and/or pharmaceutically acceptable salt(s) thereof and thus increase impurity levels in the solution. Thus, in some embodiments, some or all of the oxygen present in the water may be removed by sparging the water with an inert gas, such as argon or nitrogen. The water may be sparged at any point during the manufacturing process, including prior to combination with the hydromorphone and/or pharmaceutically acceptable salt(s) thereof, after the hydromorphone and/or pharmaceutically acceptable salt(s) thereof has dissolved, after the concentration of the hydromorphone and/or pharmaceutically acceptable salt(s) thereof in the solution has been adjusted by further additions, or any combination thereof. In order to reduce the presence of unwanted oxygen, the hydromorphone solution may optionally be held under a blanket of inert gas, such as argon or nitrogen, during the manufacturing process and prior to inserting the solution into a container. Additionally, an inert gas may be added or injected into the headspace of the container, to further purge oxygen therefrom.

Following manufacture, the hydromorphone solution may be aseptically inserted into a container, such as an ampoule, vial, or syringe. Optionally, the solution is aseptically filtered prior to aseptically filling the container. In some embodiments, the solution may be aseptically filtered using, for example, a 0.2 µm sterile filter.

In some embodiments, the containers may be colored. Without wishing to be bound to any particular theory, it is believed exposure to light may cause or accelerate degradation of the hydromorphone and/or pharmaceutically acceptable salt(s) thereof, and thus formation of impurities and discoloration of the solution. Use of colored containers may help reduce exposure of the solution to light, thus decreasing the amount of impurity formation. Thus in some embodiments, the container is a colored container, such as an amber container.

In order to reduce or eliminate interactions between the container and the hydromorphone solution, in some embodiments, the container may be treated prior to filling to render the interior surface of the container inert. For instance, containers, and in particular glass containers, may be dealkalized in order to prevent or reduce the diffusion or exchange of ions between the solution and the glass, which may lead to alterations in the pH of the solution over time. Any suitable container treatment known in the art may be used. In one particular embodiment, the containers are treated with a sulfate, such as ammonium sulfate, prior to sterilization of the container and aseptic filling.

In one embodiment, the container is a vial. The vial can be made of glass or plastic. It may be closed off at the top by a stopper with crimp top. Flip off tops may also be used for optional tamper proof and/or color coding. Color coding may be done by concentration and/or vial size, thereby reducing practitioner error and increasing safety to the recipient. Types of stoppers that may be used include rubber and plastic. The size of the vial may be, for example, 20 ml or 40 ml. In one embodiment, the vial is an amber vial.

In other embodiments, the container is a syringe. Any syringe known in the art as suitable for intrathecal injection may be used. One exemplary syringe is set forth in FIG. 1.

Referring to FIG. 1, the syringe 10 comprises a barrel 14, a plunger 11 with attached gasket 12, and a leer-lock tip 13. The barrel 14 may be made of glass or plastic having two open ends. The syringe 10 may be of varying sizes, for example, may have sizes of 5 ml, 20 ml, or 40 ml. One end of the barrel 14 is closed off by a plunger 11 that forces the hydromorphone solution (not shown) to the other end of the barrel 14 when dispensing. A gasket 12 is attached to the plunger 11 for sealing the solution in the barrel 14. The gasket 12 may be made of a rubbery elastic material, such as natural rubber or synthetic rubber. The dispensing end of the barrel 14 is closed off by a leur-lock tip 13. The leur-lock tip 13 mates with the infusion system for dispensing the solution.

The syringe may be aseptically filled with a hydromorphone solution of the present disclosure to form a pre-filled syringe, which may be used to fill and refill infusion systems for intrathecal delivery of the hydromorphone solution. The pre-filled syringe may be formed by aseptically filling the barrel of the syringe with the hydromorphone solution of the present disclosure. The filled syringe is then aseptically sealed (e.g., capped) using any suitable technique known in the art, to form a pre-filled syringe containing sterile hydromorphone solution therein. In certain aspects, the pre-filled syringe may be subsequently inserted into an outer packaging material (e.g., box, sealed tray, etc.) and sold as a packaged pre-filled syringe.

Thus, also provided is a pre-filled syringe comprising a hydromorphone solution of the present disclosure that is ready for immediate injection of the hydromorphone solution into the intrathecal space or delivery to an infusion system. Since the syringe already contains the hydromorphone solution, the process of drawing up and filtering the composition into a syringe prior to administering the solution or filling or refilling the infusion system is eliminated. Eliminating this process makes filling and refilling the infusion system safer and easier, since a practitioner does not have to draw up and filter the solution while administering the therapy to the patient, and also avoids the potential of contamination of the solution with, for example, glass particles from an ampoule, bacteria, and the like. A practitioner merely opens the outer packaging to gain access to the pre-filled syringe, which is ready for use.

The containers and/or packaging may optionally be labeled and/or color-coded to allow for easy identification of the size of the container (e.g., the volume of solution within the container) and/or the concentration of the hydromorphone solution in the container. The containers may optionally be packaged with instructions for use.

As discussed above, the presence of oxygen may lead to oxidation of the hydromorphone or salt thereof, instability of the solution, and unwanted changes in pH. In order to reduce the chances of oxidation of the hydromorphone solutions, a blanket of inert gas, such as argon or nitrogen, may be laid across the containers before they are sealed to displace any oxygen present. Oxidation of the hydromorphone solutions in syringes may also be minimized by the lack of head space in the syringes, which limits the presence of any gasses, including oxygen, within the syringe. Thus, in another embodiment, the hydromorphone solution is stored under an inert atmosphere (e.g., nitrogen, argon) within the container. In one particular embodiment, the hydromorphone solution is stored under an intert atmosphere within a vial.

Method of Use

The hydromorphone solutions of the present disclosure can be used to facilitate management of pain that is associated with any of a wide variety of disorders, conditions, or diseases. The disclosure thus further provides methods of treating pain in a subject, comprising administering intrathecally a hydromorphone solution of the disclosure to a subject in need of pain relief or prevention. The solutions are administered intrathecally using any known technique (e.g., using a drug delivery device, such as an infusion system, or injecting by hand directly into the intrathecal space). The hydromorphone solutions are desirably suitable for use with an intrathecal infusion system. The solutions of the present disclosure are suitable for use with any intrathecal delivery system known in the art. Suitable intrathecal drug delivery systems are commercially available, and include the Medtronic SynchroMed® Infusion System, the SynchroMed® II Programmable Pump, the Johnson and Johnson Codman® division pumps, and InSet® technologies pumps.

Figure 2:
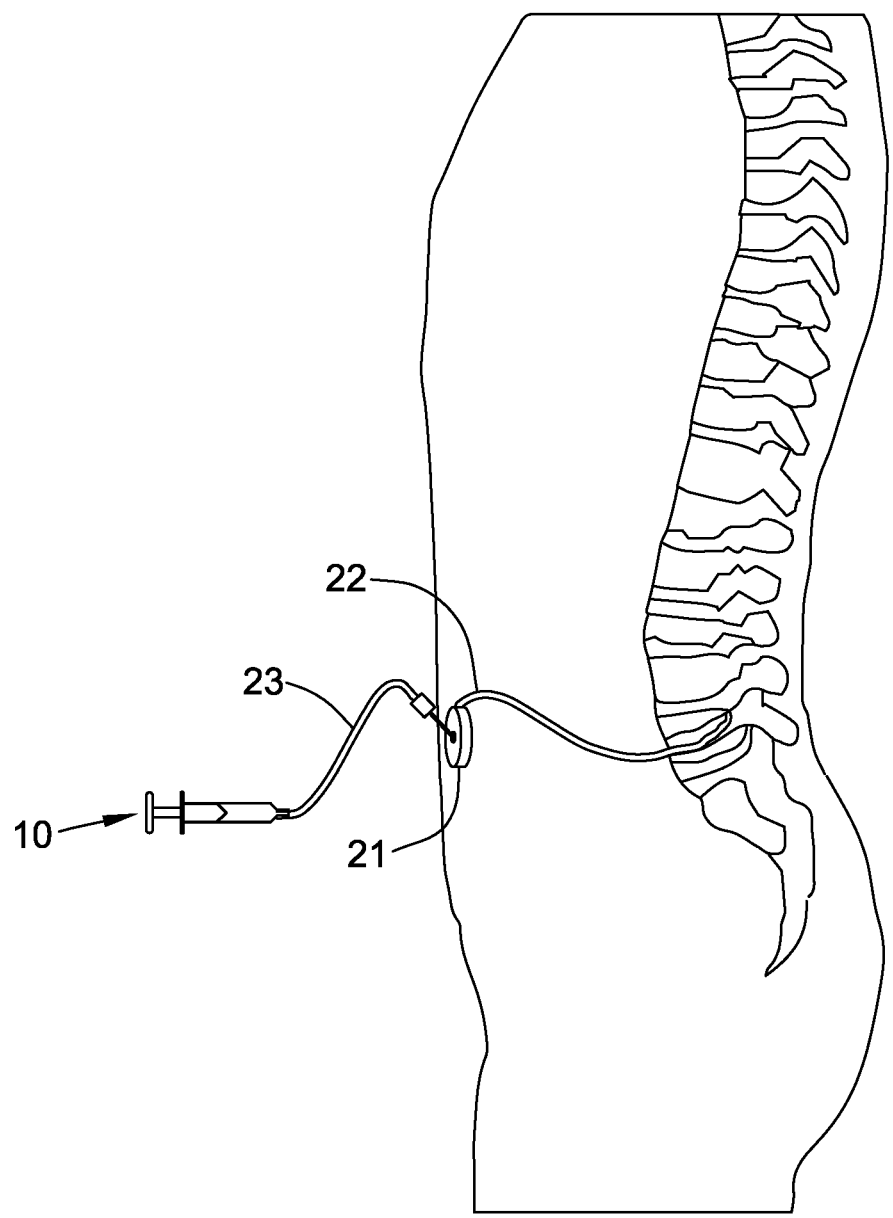
FIG. 2 is an illustration of the syringe as used with an infusion system.

One exemplary intrathecal drug delivery system is illustrated in FIG. 2, which displays a syringe 10 filled with a hydromorphone solution of the present disclosure (not shown) as used with a pump delivery system. The delivery system includes a catheter 23 for connecting the syringe to the pump 21. The hydromorphone solution may be dispensed from the syringe 10, through the catheter 23, into the pump 21. The pump 21 then pumps the hydromorphone solution through a second catheter 22 to a desired location in the body.

The methods of the present disclosure can be used to treat a variety of different types of pain. The causes of the pain may be identifiable or unidentifiable. Where identifiable, the origin of pain may be, for example, of malignant, non-malignant, infectious, non-infectious, or autoimmune origin. Of particular interest is the management of pain associated with disorders, diseases, or conditions that require long-term therapy, e.g., chronic and/or persistent diseases or conditions for which therapy involves treatment over a period of several days (e.g., about 3 days to 10 days), to several weeks (e.g., about 3 or 4 weeks to 6 weeks), to several months or years, up to including the remaining lifetime of the subject. Subjects who are not presently suffering from a disease or condition, but who are susceptible to such may also benefit from prophylactic pain management using the devices and methods of the disclosure, e.g., prior to traumatic surgery. Pain amenable to therapy according to the disclosure may involve prolonged episodes of pain alternating with pain-free intervals, or substantially unremitting pain that varies in severity.

In general, pain can be somatogenic, neurogenic, or psychogenic. Somatogenic pain can be muscular or skeletal (i.e., osteoarthritis, lumbosacral back pain, posttraumatic, myofascial), visceral (i.e., chronic pancreatitis, ulcer, irritable bowel), ischemic (i.e., arteriosclerosis obliterans), or related to the progression of cancer (e.g., malignant or non-malignant). Neurogenic pain can be due to posttraumatic and postoperative neuralgia, can be related to neuropathies (i.e., diabetes, toxicity, etc.), and can be related to nerve entrapment, facial neuralgia, perineal neuralgia, post-amputation, thalamic, causalgia, and reflex sympathetic dystrophy.

Specific examples of conditions, diseases, disorders, and origins of pain amenable to management according to the present disclosure include, but are not necessarily limited to, cancer pain (e.g., metastatic or non-metastatic cancer), chronic inflammatory disease pain, neuropathic pain, post-operative pain, iatrogenic pain (e.g., pain following invasive procedures or high dose radiation therapy, e.g., involving scar tissue formation resulting in a debilitating compromise of freedom of motion and substantial chronic pain), complex regional pain syndromes, failed-back pain (chronic back pain), soft tissue pain, joints and bone pain, central pain, injury (e.g., debilitating injuries, e.g., paraplegia, quadriplegia, etc., as well as non-debilitating injury (e.g., to back, neck, spine, joints, legs, arms, hands, feet, etc.), arthritic pain (e.g., rheumatoid arthritis, osteoarthritis, arthritic symptoms of unknown etiology, etc.), hereditary disease (e.g., sickle cell anemia), infectious disease and resulting syndromes (e.g., Lyme disease, AIDS, etc.), chronic headaches (e.g., migraines), causalgia, hyperesthesia, sympathetic dystrophy, phantom limb syndrome, denervation, and the like. Pain can be associated with any portion(s) of the body, e.g., the musculoskeletal system, visceral organs, skin, nervous system, etc.

Pain associated with any type of malignant or non-malignant cancer is amenable to alleviation according to the disclosure. Specific examples of cancers that can be associated with pain (due to the nature of the cancer itself or therapy to treat the cancer) include, but are not necessarily limited to lung cancer, bladder cancer, melanoma, bone cancer, multiple myeloma, brain cancer, non-Hodgkin's lymphoma, breast cancer, oral cancers, cervical cancer, ovarian cancer, colon cancer, rectal cancer, pancreatic cancer, dysplastic nevi, endocrine cancer, prostate cancer, head and neck cancers, sarcoma, Hodgkin's disease, skin cancer, kidney cancer, stomach cancer, leukemia, testicular cancer, liver cancer, uterine cancer, and aplastic anemia. Certain types of neuropathic pain can also be amenable to treatment according to the disclosure.

Chronic back pain, which is also amenable to management using the methods of the disclosure, is another broad category of pain that can be alleviated by application of the methods of the disclosure. Chronic back pain is generally due to one or more of the following six causes: (i) stress on intervertebral facet joints, caused by slippage, arthritis, wedging, or scoliosis; (ii) radiculopathy, the mechanical compression of the nerve root due to bulging discs or tumors; (iii) tendonitis or tendon sprain; (iv) muscle spasm or muscle sprain; (v) ischemia, a local insufficiency in circulatory flow; and (vi) neuropathy, damage to nervous tissue of metabolic etiology or arising from cord tumors or central nervous system disease.

The hydromorphone solutions may be administered at any dosage regimen suitable for treating the pain. The solution may be administered continuously and/or at intervals over a pre-selected administration period ranging from several hours, one to several weeks, one to several months, up to one or more years. In one embodiment, the solution is administered in an amount sufficient so as to provide a dose of hydromorphone and/or pharmaceutically acceptable salt(s) thereof of from about 0.5 mg/day to about 4 mg/day. When administered using an infusion system, the solution may be administered at any suitable infusion rate, including at an infusion rate of from about 0.05 ml/day to about 0.4 ml/day, including from about 0.05 ml/day to about 0.1 ml/day.

In one aspect, disclosed herein is a method of treating pain by administration of a sterile aqueous solution of hydromorphone hydrochloride, wherein said solution is substantially free of buffer or other additives.

Definitions

As used herein, the terms below have the meanings indicated.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "sterile," as used herein in reference to the claimed solutions, means the solution meets or exceeds the standards for sterility set forth in the United States Pharmacopeia (USP). In certain particular embodiments, a sterile solution of the present disclosure is free from all detectable live bacteria or other microorganisms and their spores. The sterility of the compositions of the present disclosure may be tested using any suitable technique known in the art.

The term "particulate," as used herein, is meant to describe undissolved particles, other than gas bubbles, unintentionally present in the drug solution.

The term "intrathecal," as used herein, means introduced into or occurring in the space under the arachnoid membrane which covers the brain and spinal cord. Intrathecal drug delivery is designed to manage chronic pain and/or spasticity, such as intractable cancer pain, by delivering pain medication directly to the intrathecal space. Intrathecal drug delivery typically uses an implantable infusion system to deliver pain medication directly to the intrathecal space via a surgically implanted infusion pump and catheter, but also refers to direct injection of the drug into the intrathecal space using a syringe (e.g., injected by hand).

The term "stable" as used herein in reference to the disclosed solutions means retaining substantially the same properties and characteristics throughout its period of storage and use that it possessed at the time of its manufacture, such that the solution or composition provides substantially the same therapeutic benefit to the patient over the period of time that the solution is stored and delivered, such as for about 1 month, about 3 months, about 6 months, about 1 year, or about 2 years. For example, in particular embodiments, the solutions or compositions disclosed herein are stable if they contain within 3% of the amount of hydromorphone hydrochloride as claimed on the label (% LC) after about 12 weeks, as determined by HPLC assay.

The term "active pharmaceutical ingredient" or "API," as used herein, means any substance that may be used in a pharmaceutical product, and which is intended to furnish, alone or in combination with another substance, pharmacological activity or to otherwise have direct effect in the diagnosis, cure, mitigation, treatment or prevention of disease, or to have direct effect in restoring, correcting, or modifying physiological functions in human beings or other mammals.

The term "substantially free of", when used in connection with the solutions of the present disclosure, means the indicated substance (e.g., a buffer or an "other additive") has not been affirmatively added to the solution during manufacture of the solution.

As used herein, "other additives" generally refers to and includes any other additives, components or agents that may be affirmatively added to the solutions of the present disclosure, including those that have been known to be included in pharmaceutical compositions or solutions—such as hydromorphone solutions. Additives that may optionally be excluded from, and thus not added to, the solutions of the disclosure may include, without limitation: an active pharmaceutical ingredient ("API") other than hydromorphone or pharmaceutically acceptable salt(s) of hydromorphone; acids; pH adjusters; preservatives; polymeric materials; emulsifiers; lubricants; antioxidants; suspending agents; excipients (other than water); diluents; oils; surfactants; saline; solvents; metal salts; minerals; vitamins; sterilizers; and stabilizers; and any combination thereof.

"Subject" when used in connection with the methods of treatment disclosed herein refers to a human or other mammal.

"Treatment" as in "treatment of pain" is used herein to encompass both a decrease in pain severity and/or intensity to provide partial or complete relief of pain and/or pain symptoms. The effect may be prophylactic in terms of completely or partially preventing or reducing the severity of pain.

The term "pain management" is used here to generally describe regression, suppression, or mitigation of pain, including acute and chronic pain, so as to make the subject more comfortable as determined by subjective criteria, objective criteria, or both. In general, pain is assessed subjectively by patient report, with the health professional taking into consideration the patient's age, cultural background, environment, and other psychological background factors known to alter a person's subjective reaction to pain.

The term "aqueous" as used herein in reference to the hydromorphone solutions means the solutions contain water.

Certain embodiments disclosed herein may be illustrated by the following non-limiting examples.

Example 1

Preparation of 10.0 Mg/mL Hydromorphone Hydrochloride Solution with 0.2% Citrate Buffer To 1 L of water for injection (WFI) is added 40.4 g citrate buffer, and the mixture is stirred for 10±2 minutes. To the resulting solution is added 200.0 g hydromorphone hydrochloride and 2 L WFI. The mixture is then stirred for 45 minutes. The resulting solution is diluted to 20 L with WFI and stirred for at least an additional 10 minutes.

Example 2

Preparation of 10.0 Mg/mL Hydromorphone Hydrochloride Solution with 0.1% Citrate Buffer To 1 L of WFI is added 20.2 g citrate buffer, and the mixture is stirred for 10±2 minutes. To the resulting solution is added 200.0 g hydromorphone hydrochloride and 2 L WFI. The mixture is then stirred for 45 minutes. The resulting solution is diluted to 20 L with WFI and stirred for at least an additional 10 minutes.

Example 3

Preparation of 10.0 Mg/mL Hydromorphone Hydrochloride Solution with 0.05% Citrate Buffer To 1 L of WFI is added 10.1 g citrate buffer, and the mixture is stirred for 10±2 minutes. To the resulting solution is added 200.0 g hydromorphone hydrochloride and 2 L WFI. The mixture is then stirred for 45 minutes. The resulting solution is diluted to 20 L with WFI and stirred for at least an additional 10 minutes.

Example 4

Preparation of 10.0 Mg/mL Hydromorphone Hydrochloride Solution with 0.03% Citrate Buffer To 1 L of WFI is added 6.06 g citrate buffer, and the mixture is stirred for 10±2 minutes. To the resulting solution is added 200.0 g hydromorphone hydrochloride and 2 L WFI. The mixture is then stirred for 45 minutes. The resulting solution is diluted to 20 L with WFI and stirred for at least an additional 10 minutes.

Example 5

Preparation of 10.0 mg/mL Hydromorphone Hydrochloride Solution with 0% Citrate Buffer To 3 L of WFI is added 200.0 g hydromorphone hydrochloride. The mixture is stirred for 45 minutes. The resulting solution is diluted to 20 L with WFI and stirred for at least an additional 10 minutes.

Example 6

Impurity Profile of Hydromorphone Hydrochloride Solutions with Varying Amounts of Buffer The impurity profile of the compositions produced in Examples 1-5, showing the amount of each impurity, as well as the percent of the label claim (% LC) of the API, as determined by HPLC assay.

| Buffer-containing Solutions | | | | | | | |
|---|---|---|---|---|---|---|---|
| % Buffer | pH | % L.C. | % HNO | % DHM | % THO | %0.56 RRT | % Pseudo-HM |
| 0 | 5.0 | 99.0 | <0.05 | <0.05 | <0.05 | <0.05 | <0.05 |
| 0.03 | 4.2 | 100.4 | <0.05 | <0.05 | <0.05 | <0.05 | <0.05 |
| 0.05 | 4.1 | 101.1 | <0.05 | <0.05 | <0.05 | <0.05 | <0.05 |
| 0.1 | 4.1 | 100.7 | <0.05 | <0.05 | <0.05 | <0.05 | 0.05 |
| 0.2 | 4.1 | 100.1 | <0.05 | <0.05 | <0.05 | <0.05 | <0.05 |

Example 7

Impurity Profile of Hydromorphone Hydrochloride Solution with 0% Buffer Over Time The impurity profile of the composition prepared in Example 5 over time, showing the amount of each impurity, as well as the percent of the label claim (% LC) of the hydromorphone HCl, as determined by HPLC assay.

| Time (Days) | pH | % L.C. | % HNO | % DHM | % THO | % Pseudo-HM |
|---|---|---|---|---|---|---|
| 0 | 5.0 | 99.0 | <0.05 | <0.05 | <0.05 | <0.05 |
| 3 | — | 97.7 | <0.05 | <0.05 | <0.05 | <0.05 |
| 7 | — | 99.7 | <0.05 | <0.05 | <0.05 | <0.05 |
| 14 | 4.6 | 102.4 | <0.05 | <0.05 | <0.05 | 0.06 |
| 28 | 4.6 | 99.3 | <0.05 | <0.05 | <0.05 | 0.07 |
| 56 | 4.6 | 99.0 | <0.05 | <0.05 | <0.05 | 0.07 |
| 84 | 4.5 | 100.5 | <0.05 | <0.05 | <0.05 | 0.09 |

The data shows that compositions containing buffer have the same levels of impurities as the composition without buffer. This indicates that the buffer is not an essential part of the composition from an impurity standpoint. Further, additional data shows that the buffer-free composition maintains its low levels of impurities over time, indicating that buffer is not essential to the long-term stability of the composition.

The formulation without buffer has a small pH change (only 0.5 pH units) over the time period tested. This indicates that the buffer is not necessary to keep the pH stable over time. This pH data, coupled with the impurity data, shows that the small change in pH that is observed does not have a detrimental effect on the purity of the formulation. Further, the absence of the buffer gives the formulation a pH closer to the patient's natural physiological pH of the cerebrospinal fluid than the formulation containing the buffer (5.0 vs. 4.1).

Example 8

Effect of Terminal Sterilization on Impurity Formation

The effect of terminal sterilization on the formation of impurities was evaluated for hydromorphone HCl solutions containing varying amounts of citrate buffer.

Five batches (400 L each) of hydromorphone HCl solutions (solutions A-E) having a concentration of hydromorphone HCl of 10 mg/ml were prepared using varying amounts of citrate buffer and WFI (obtained from Steriles South). WFI was added to a compounding tank and mixing was started. The WFI was sparged with nitrogen to remove dissolved oxygen present in the WFI. For solutions containing citrate buffer, citrate buffer was added to the tank in an amount sufficient to obtain the desired final concentration of buffer, and the resulting mixture was stirred for 10±2 minutes. Hydromorphone HCl was added to the resulting mixture (or to WFI if no citrate buffer was used), and the mixture was stirred until the hydromorphone HCl was dissolved and the mixture was homogenous. Once dissolved and homogenous, the mixture was again sparged with nitrogen. The resulting solutions were diluted with WFI to obtain a concentration of hydromorphone HCl of 10 mg/ml, and stirred for at least an additional 10 minutes. The solutions were again sparged with nitrogen, and filtered into a holding tank. A nitrogen blanket was maintained during the hold period prior to container filling.

The solutions were used to fill amber 20 cc glass vials. A 20 cc rubber vial stopper (available from West) and flip top aluminum crimp (available from West) were used as the container closure system. The filled containers were either terminally sterilized (TS) or withheld from terminal sterilization (non-terminally sterilized, NTS). The containers subjected to terminal sterilization were sterilized for 20 minutes at 121° C. or greater. A summary of the manufacture of solutions A-E is set forth in Table 1 below:

TABLE 1

| Solution | % citrate buffer | pH prior to HM HCl addition | Final pH | Total vials filled | Sterilization parameters |
|---|---|---|---|---|---|
| A | 0.20% | 3.75 | 3.77 | 180 | TS, NTS |
| B | None | 5.48 | 4.80 | 60 | TS, NTS |
| C | 0.03% | 4.09 | 3.83 | 60 | TS, NTS |
| D | 0.05% | 4.10 | 3.95 | 60 | TS, NTS |
| E | 0.10% | 4.17 | 4.03 | 60 | TS, NTS |

HM HCl = hydromorphone HCl;
TS = terminally sterilized;
NTS = non-terminally sterilized 125 commercially available samples of hydromorphone HCl (10 mg/ml) were also purchased from Best Value Drugs (Farmville, N.C.).

The commercially available sample and solutions A-E were tested at day 0 (i.e., the day solutions A-E were prepared) for stability (% LC) and impurities using high performance liquid chromatography (HPLC). The percentage of unknown impurities that eluted from the HPLC column at a relative retention time (RRT) of 0.56 and 0.80 (relative to the hydromorphone HCl peak elution time) was also measured. The results are set forth in Table 2 below.

TABLE 2

| | | | | Day 0 | | | | | | | |
|---|---|---|---|---|---|---|---|---|---|---|---|
| Solution | TS or NTS | Citrate Buffer | pH | LC (%) | HNO (%) | DHM (%) | THO (%) | 0.56 RRT (%) | 0.80 RRT (%) | PHM (%) | Total Impurity (%) |
| Commercial* | — | Yes | 4.1 | 100.4 | <0.05 | <0.05 | <0.05 | <0.05 | 0.07 | 0.51 | 0.58 |
| A | NTS | 0.2% | 4.1 | 100.1 | <0.05 | <0.05 | <0.05 | <0.05 | <0.05 | <0.05 | 0.00 |
| A | TS | 0.2% | 4.1 | 100.2 | <0.05 | <0.05 | <0.05 | <0.05 | 0.21 | 0.09 | 0.30 |
| B | NTS | 0% | 5.0 | 99.0 | <0.05 | <0.05 | <0.05 | <0.05 | <0.05 | <0.05 | 0.00 |
| B | TS | 0% | 5.0 | 100.5 | <0.05 | <0.05 | <0.05 | <0.05 | 0.25 | 0.41 | 0.66 |
| C | NTS | 0.03% | 4.2 | 100.4 | <0.05 | <0.05 | <0.05 | <0.05 | <0.05 | <0.05 | 0.00 |
| C | TS | 0.03% | 4.2 | 100.7 | <0.05 | <0.05 | <0.05 | <0.05 | 0.24 | 0.25 | 0.49 |
| D | NTS | 0.05% | 4.1 | 101.1 | <0.05 | <0.05 | <0.05 | <0.05 | <0.05 | <0.05 | 0.00 |
| D | TS | 0.05% | 4.2 | 100.3 | <0.05 | <0.05 | <0.05 | <0.05 | 0.31 | 0.29 | 0.60 |
| E | NTS | 0.10% | 4.1 | 100.7 | <0.05 | <0.05 | <0.05 | <0.05 | <0.05 | 0.05 | 0.05 |
| E | TS | 0.10% | 4.1 | 100.8 | <0.05 | <0.05 | <0.05 | <0.05 | 0.18 | 0.09 | 0.27 |

LC = label claim; HNO = hydromorphone N-oxide; DHM = dihydromorphine; THO = 6-β-tetrahydrooripavine; RRT = relative retention time; PHM = pseudo-hydromorphone
*The sterilization method for the commercial samples was unknown at day 0. The commercial samples contained 0.2% sodium citrate and 0.2% citric acid.

As can be seen from Table 2, the pH of the solutions at day 0 ranged from 4.1 to 5.0. Solution B, which contained no citrate buffer, had the highest pH (i.e., pH 5.0), further demonstrating that the absence of buffer gives the solution a pH closer to the natural physiological pH of cerebrospinal fluid than the solutions containing buffer (e.g. compositions A and C-E and the commercial composition). The assay values for percent label claim (% LC) of hydromorphone HCl ranged from 99.0% to 100.8%, which are all comparable and within normal analytical variance. The levels of the known impurity pseudo-hydromorphone (PHM), unknown impurities at 0.80 RRT, and total impurities were higher in the terminally sterilized products when compared to the non-terminally sterilized products. These results suggest that terminal sterilization of the hydromorphone HCl solutions adversely impacts stability of the solutions.

Example 9

Effect of Terminal Sterilization and Storage Conditions on Stability and Impurity Formation The effect of terminal sterilization and storage conditions on solution stability and the formation of impurities was evaluated for hydromorphone HCl solutions containing varying amounts of citrate buffer.

Terminally sterilized samples of solutions A-E from Example 8 were stored either upright or inverted at 25° C., 30° C. or 40° C., and tested for stability (% LC) and impurities 3, 7, 14, 28, 56, and 84 days after manufacture. The commercially available composition from Example 8 was also tested. The results were compared to those obtained for a non-terminally sterilized sample of solution B (containing no citrate buffer). The results are set forth in Tables 3-8 below.

TABLE 3

Day 3

| Solution | TS or NTS | Citrate Buffer | U or I | Storage Temp (° C.) | pH | LC (%) | HNO (%) | DHM (%) | THO (%) | 0.56 RRT (%) | 0.80 RRT (%) | PHM (%) | Total Impurity (%) |
|---|---|---|---|---|---|---|---|---|---|---|---|---|---|
| Commercial | — | Yes | U | 25 | 4.0 | 99.4 | <0.05 | <0.05 | <0.05 | <0.05 | 0.08 | 0.49 | 0.57 |
| Commercial | — | Yes | I | 25 | n/a | 97.5 | <0.05 | <0.05 | <0.05 | <0.05 | 0.08 | 0.49 | 0.57 |
| A | TS | 0.2% | U | 25 | n/a | 98.8 | <0.05 | <0.05 | <0.05 | <0.05 | 0.20 | 0.08 | 0.28 |
| A | TS | 0.2% | I | 25 | n/a | 99.5 | <0.05 | <0.05 | <0.05 | <0.05 | 0.20 | 0.08 | 0.28 |
| B | TS | 0.0% | U | 25 | 4.5 | 99.0 | <0.05 | <0.05 | <0.05 | <0.05 | 0.31 | 0.49 | 0.80 |
| C | TS | 0.03% | U | 25 | 4.0 | 98.8 | <0.05 | <0.05 | <0.05 | <0.05 | 0.25 | 0.23 | 0.48 |
| D | TS | 0.05% | U | 25 | 3.9 | 99.4 | <0.05 | <0.05 | <0.05 | <0.05 | 0.18 | 0.19 | 0.37 |
| E | TS | 0.10% | U | 25 | 3.9 | 99.3 | <0.05 | <0.05 | <0.05 | <0.05 | 0.18 | 0.07 | 0.25 |
| Commercial | — | Yes | U | 30 | 4.0 | 99.0 | <0.05 | <0.05 | <0.05 | <0.05 | 0.07 | 0.50 | 0.57 |
| Commercial | — | Yes | I | 30 | n/a | 98.9 | <0.05 | <0.05 | <0.05 | <0.05 | 0.07 | 0.55 | 0.62 |
| A | TS | 0.2% | U | 30 | n/a | 96.6 | <0.05 | <0.05 | <0.05 | <0.05 | 0.23 | 0.10 | 0.33 |
| A | TS | 0.2% | I | 30 | n/a | 99.5 | <0.05 | <0.05 | <0.05 | <0.05 | 0.20 | 0.09 | 0.29 |
| B | TS | 0.0% | U | 30 | 4.5 | 97.2 | <0.05 | <0.05 | <0.05 | <0.05 | 0.26 | 0.42 | 0.68 |
| C | TS | 0.03% | U | 30 | 4.0 | 98.8 | <0.05 | <0.05 | <0.05 | <0.05 | 0.34 | 0.29 | 0.63 |
| D | TS | 0.05% | U | 30 | 3.9 | 99.9 | <0.05 | <0.05 | <0.05 | <0.05 | 0.20 | 0.16 | 0.36 |
| E | TS | 0.10% | U | 30 | 3.9 | 99.4 | <0.05 | <0.05 | <0.05 | <0.05 | 0.19 | 0.11 | 0.30 |
| Commercial | — | Yes | U | 40 | 4.0 | 98.9 | <0.05 | <0.05 | <0.05 | <0.05 | 0.08 | 0.50 | 0.58 |
| Commercial | — | Yes | I | 40 | n/a | 99.9 | <0.05 | <0.05 | <0.05 | <0.05 | 0.08 | 0.51 | 0.59 |
| A | TS | 0.2% | U | 40 | n/a | 99.3 | <0.05 | <0.05 | <0.05 | <0.05 | 0.19 | 0.07 | 0.26 |
| A | TS | 0.2% | I | 40 | n/a | 99.4 | <0.05 | <0.05 | <0.05 | <0.05 | 0.25 | 0.11 | 0.36 |
| B | TS | 0.0% | U | 40 | 4.5 | 97.5 | <0.05 | <0.05 | <0.05 | <0.05 | 0.25 | 0.42 | 0.67 |
| C | TS | 0.03% | U | 40 | 4.0 | 98.2 | <0.05 | <0.05 | <0.05 | <0.05 | 0.30 | 0.27 | 0.57 |
| D | TS | 0.05% | U | 40 | 3.9 | 97.9 | <0.05 | <0.05 | <0.05 | <0.05 | 0.29 | 0.23 | 0.52 |
| E | TS | 0.10% | U | 40 | 3.9 | 99.4 | <0.05 | <0.05 | <0.05 | <0.05 | 0.19 | 0.07 | 0.26 |
| B | NTS | 0.0% | — | — | n/a | 97.7 | <0.05 | <0.05 | <0.05 | <0.05 | <0.05 | <0.05 | 0.00 |

I = inverted; U = upright

TABLE 4

Day 7

| Solution | TS or NTS | Citrate Buffer | U or I | Storage Temp (° C.) | pH | LC (%) | HNO (%) | DHM (%) | THO (%) | 0.56 RRT (%) | 0.80 RRT (%) | PHM (%) | Total Impurity (%) |
|---|---|---|---|---|---|---|---|---|---|---|---|---|---|
| Commercial | — | Yes | U | 25 | 4.0 | 99.3 | <0.05 | <0.05 | <0.05 | <0.05 | <0.05 | 0.52 | 0.52 |
| Commercial | — | Yes | I | 25 | n/a | 98.3 | <0.05 | <0.05 | <0.05 | <0.05 | <0.05 | 0.52 | 0.52 |
| A | TS | 0.2% | U | 25 | n/a | 98.7 | <0.05 | <0.05 | <0.05 | <0.05 | 0.15 | 0.09 | 0.24 |
| A | TS | 0.2% | I | 25 | n/a | 98.0 | <0.05 | <0.05 | <0.05 | <0.05 | 0.15 | 0.09 | 0.24 |
| B | TS | 0.0% | U | 25 | 4.6 | 99.0 | <0.05 | <0.05 | <0.05 | <0.05 | 0.21 | 0.43 | 0.64 |
| C | TS | 0.03% | U | 25 | 4.0 | 99.4 | <0.05 | <0.05 | <0.05 | <0.05 | 0.18 | 0.23 | 0.41 |

TABLE 4-continued

Day 7

| Solution | TS or NTS | Citrate Buffer | U or I | Storage Temp (° C.) | pH | LC (%) | HNO (%) | DHM (%) | THO (%) | 0.56 RRT (%) | 0.80 RRT (%) | PHM (%) | Total Impurity (%) |
|---|---|---|---|---|---|---|---|---|---|---|---|---|---|
| D | TS | 0.05% | U | 25 | 3.9 | 99.7 | <0.05 | <0.05 | <0.05 | <0.05 | 0.16 | 0.18 | 0.34 |
| E | TS | 0.10% | U | 25 | 3.9 | 98.3 | <0.05 | <0.05 | <0.05 | <0.05 | 0.13 | 0.07 | 0.20 |
| Commercial | — | Yes | U | 30 | 4.0 | 100.0 | <0.05 | <0.05 | <0.05 | <0.05 | <0.05 | 0.52 | 0.52 |
| Commercial | — | Yes | I | 30 | n/a | 100.0 | <0.05 | <0.05 | <0.05 | <0.05 | <0.05 | 0.51 | 0.51 |
| A | TS | 0.2% | U | 30 | n/a | 99.9 | <0.05 | <0.05 | <0.05 | <0.05 | 0.14 | 0.08 | 0.22 |
| A | TS | 0.2% | I | 30 | n/a | 97.7 | <0.05 | <0.05 | <0.05 | <0.05 | 0.15 | 0.09 | 0.24 |
| B | TS | 0.0% | U | 30 | 4.5 | 98.8 | <0.05 | <0.05 | <0.05 | <0.05 | 0.19 | 0.41 | 0.60 |
| C | TS | 0.03% | U | 30 | 4.0 | 99.8 | <0.05 | <0.05 | <0.05 | <0.05 | 0.26 | 0.28 | 0.54 |
| D | TS | 0.05% | U | 30 | 3.9 | 98.4 | <0.05 | <0.05 | <0.05 | <0.05 | 0.20 | 0.22 | 0.42 |
| E | TS | 0.10% | U | 30 | 3.9 | 100.0 | <0.05 | <0.05 | <0.05 | <0.05 | 0.13 | 0.08 | 0.21 |
| Commercial | — | Yes | U | 40 | 4.0 | 99.9 | <0.05 | <0.05 | <0.05 | <0.05 | <0.05 | 0.52 | 0.52 |
| Commercial | — | Yes | I | 40 | n/a | 99.9 | <0.05 | <0.05 | <0.05 | <0.05 | <0.05 | 0.52 | 0.52 |
| A | TS | 0.2% | U | 40 | n/a | 98.1 | <0.05 | <0.05 | <0.05 | <0.05 | 0.16 | 0.11 | 0.27 |
| A | TS | 0.2% | I | 40 | n/a | 98.5 | <0.05 | <0.05 | <0.05 | <0.05 | 0.16 | 0.10 | 0.26 |
| B | TS | 0.0% | U | 40 | 4.5 | 99.6 | <0.05 | <0.05 | <0.05 | <0.05 | 0.20 | 0.42 | 0.62 |
| C | TS | 0.03% | U | 40 | 4.0 | 98.5 | <0.05 | <0.05 | <0.05 | <0.05 | 0.16 | 0.22 | 0.38 |
| D | TS | 0.05% | U | 40 | 3.9 | 99.6 | <0.05 | <0.05 | <0.05 | <0.05 | 0.15 | 0.20 | 0.35 |
| E | TS | 0.10% | U | 40 | 3.9 | 99.5 | <0.05 | <0.05 | <0.05 | <0.05 | 0.13 | 0.09 | 0.22 |
| B | NTS | 0.0% | — | — | n/a | 99.7 | <0.05 | <0.05 | <0.05 | <0.05 | <0.05 | <0.05 | 0.00 |

TABLE 5

Day 14

| Solution | TS or NTS | Citrate Buffer | U or I | Storage Temp (° C.) | pH | LC (%) | HNO (%) | DHM (%) | THO (%) | 0.56 RRT (%) | 0.80 RRT (%) | PHM (%) | Total Impurity (%) |
|---|---|---|---|---|---|---|---|---|---|---|---|---|---|
| Commercial | — | Yes | U | 25 | 4.0 | 98.9 | <0.05 | <0.05 | <0.05 | <0.05 | <0.05 | 0.51 | 0.51 |
| Commercial | — | Yes | I | 25 | 4.0 | 101.7 | <0.05 | <0.05 | <0.05 | <0.05 | <0.05 | 0.51 | 0.51 |
| A | TS | 0.2% | U | 25 | 3.9 | 100.7 | <0.05 | <0.05 | <0.05 | <0.05 | 0.20 | 0.14 | 0.34 |
| A | TS | 0.2% | I | 25 | 3.9 | 98.5 | <0.05 | <0.05 | <0.05 | <0.05 | 0.17 | 0.14 | 0.31 |
| B | TS | 0.0% | U | 25 | 4.5 | 100.0 | <0.05 | <0.05 | <0.05 | <0.05 | 0.26 | 0.46 | 0.72 |
| C | TS | 0.03% | U | 25 | 3.9 | 100.4 | <0.05 | <0.05 | <0.05 | <0.05 | 0.22 | 0.26 | 0.48 |
| D | TS | 0.05% | U | 25 | 3.9 | 100.7 | <0.05 | <0.05 | <0.05 | <0.05 | 0.21 | 0.22 | 0.43 |
| E | TS | 0.10% | U | 25 | 3.9 | 99.8 | <0.05 | <0.05 | <0.05 | <0.05 | 0.18 | 0.10 | 0.28 |
| Commercial | — | Yes | U | 30 | 4.0 | 100.1 | <0.05 | <0.05 | <0.05 | <0.05 | <0.05 | 0.50 | 0.50 |
| Commercial | — | Yes | I | 30 | 4.0 | 100.5 | <0.05 | <0.05 | <0.05 | <0.05 | <0.05 | 0.50 | 0.50 |
| A | TS | 0.2% | U | 30 | 3.9 | 100.0 | <0.05 | <0.05 | <0.05 | <0.05 | 0.18 | 0.12 | 0.30 |
| A | TS | 0.2% | I | 30 | 3.9 | 101.8 | <0.05 | <0.05 | <0.05 | <0.05 | 0.18 | 0.15 | 0.33 |
| B | TS | 0.0% | U | 30 | 4.5 | 100.6 | <0.05 | <0.05 | <0.05 | <0.05 | 0.22 | 0.45 | 0.67 |
| C | TS | 0.03% | U | 30 | 3.9 | 99.5 | <0.05 | <0.05 | <0.05 | <0.05 | 0.21 | 0.25 | 0.46 |
| D | TS | 0.05% | U | 30 | 3.9 | 101.9 | <0.05 | <0.05 | <0.05 | <0.05 | 0.19 | 0.21 | 0.40 |
| E | TS | 0.10% | U | 30 | 3.9 | 101.7 | <0.05 | <0.05 | <0.05 | <0.05 | 0.15 | 0.12 | 0.27 |
| Commercial | — | Yes | U | 40 | 4.0 | 101.6 | <0.05 | <0.05 | <0.05 | <0.05 | 0.05 | 0.51 | 0.56 |
| Commercial | — | Yes | I | 40 | 4.0 | 100.1 | <0.05 | <0.05 | <0.05 | <0.05 | 0.06 | 0.53 | 0.59 |
| A | TS | 0.2% | U | 40 | 3.9 | 101.2 | <0.05 | <0.05 | <0.05 | <0.05 | 0.19 | 0.13 | 0.32 |
| A | TS | 0.2% | I | 40 | 3.9 | 102.0 | <0.05 | <0.05 | <0.05 | <0.05 | 0.21 | 0.13 | 0.34 |
| B | TS | 0.0% | U | 40 | 4.4 | 100.8 | <0.05 | <0.05 | <0.05 | <0.05 | 0.25 | 0.45 | 0.70 |
| C | TS | 0.03% | U | 40 | 4.0 | 101.1 | <0.05 | <0.05 | <0.05 | <0.05 | 0.21 | 0.25 | 0.46 |
| D | TS | 0.05% | U | 40 | 4.0 | 101.1 | <0.05 | <0.05 | <0.05 | <0.05 | 0.19 | 0.22 | 0.41 |
| E | TS | 0.10% | U | 40 | 3.9 | 101.9 | <0.05 | <0.05 | <0.05 | <0.05 | 0.18 | 0.11 | 0.29 |
| B | NTS | 0.0% | — | — | 4.6 | 102.4 | <0.05 | <0.05 | <0.05 | <0.05 | <0.05 | 0.06 | 0.06 |

TABLE 6

Day 28

| Solution | TS or NTS | Citrate Buffer | U or I | Storage Temp (° C.) | pH | LC (%) | HNO (%) | DHM (%) | THO (%) | 0.56 RRT[1] (%) | 0.80 RRT[2] (%) | PHM (%) | Total Impurity (%) |
|---|---|---|---|---|---|---|---|---|---|---|---|---|---|
| Commercial | — | Yes | U | 25 | 4.0 | 99.8 | <0.05 | <0.05 | <0.05 | <0.05 | 0.06 | 0.47 | 0.53 |
| Commercial | — | Yes | I | 25 | 4.0 | 99.9 | <0.05 | <0.05 | <0.05 | <0.05 | 0.07 | 0.49 | 0.56 |
| A | TS | 0.2% | U | 25 | 3.9 | 99.7 | <0.05 | <0.05 | <0.05 | <0.05 | 0.15 | 0.08 | 0.23 |

TABLE 6-continued

Day 28

| Solution | TS or NTS | Citrate Buffer | U or I | Storage Temp (° C.) | pH | LC (%) | HNO (%) | DHM (%) | THO (%) | 0.56 RRT[1] (%) | 0.80 RRT[2] (%) | PHM (%) | Total Impurity (%) |
|---|---|---|---|---|---|---|---|---|---|---|---|---|---|
| A | TS | 0.2% | I | 25 | 3.9 | 100.7 | <0.05 | <0.05 | <0.05 | <0.05 | 0.17 | 0.09 | 0.26 |
| B | TS | 0.0% | U | 25 | 4.5 | 100.2 | <0.05 | <0.05 | <0.05 | <0.05 | 0.27 | 0.49 | 0.81 |
| C | TS | 0.03% | U | 25 | 3.9 | 99.5 | <0.05 | <0.05 | <0.05 | <0.05 | 0.25 | 0.27 | 0.57 |
| D | TS | 0.05% | U | 25 | 3.9 | 100.7 | <0.05 | <0.05 | <0.05 | <0.05 | 0.16 | 0.18 | 0.34 |
| E | TS | 0.10% | U | 25 | 3.9 | 99.5 | <0.05 | <0.05 | <0.05 | <0.05 | 0.15 | 0.10 | 0.25 |
| Commercial | — | Yes | U | 30 | 4.0 | 99.5 | <0.05 | <0.05 | <0.05 | <0.05 | 0.06 | 0.50 | 0.56 |
| Commercial | — | Yes | I | 30 | 4.0 | 99.6 | <0.05 | <0.05 | <0.05 | <0.05 | 0.07 | 0.52 | 0.59 |
| A | TS | 0.2% | U | 30 | 3.9 | 99.7 | <0.05 | <0.05 | <0.05 | <0.05 | 0.17 | 0.10 | 0.27 |
| A | TS | 0.2% | I | 30 | 3.9 | 99.4 | <0.05 | <0.05 | <0.05 | <0.05 | 0.21 | 0.12 | 0.33 |
| B | TS | 0.0% | U | 30 | 4.4 | 99.6 | <0.05 | <0.05 | <0.05 | <0.05 | 0.24 | 0.44 | 0.68 |
| C | TS | 0.03% | U | 30 | 3.9 | 99.4 | <0.05 | <0.05 | <0.05 | 0.06 | 0.29 | 0.30 | 0.65 |
| D | TS | 0.05% | U | 30 | 3.9 | 99.6 | <0.05 | <0.05 | <0.05 | <0.05 | 0.17 | 0.20 | 0.37 |
| E | TS | 0.10% | U | 30 | 3.9 | 99.3 | <0.05 | <0.05 | <0.05 | <0.05 | 0.17 | 0.09 | 0.26 |
| Commercial | — | Yes | U | 40 | 4.0 | 100.4 | <0.05 | <0.05 | <0.05 | <0.05 | 0.09 | 0.51 | 0.60 |
| Commercial | — | Yes | I | 40 | 4.0 | 99.5 | <0.05 | <0.05 | <0.05 | <0.05 | 0.09 | 0.53 | 0.62 |
| A | TS | 0.2% | U | 40 | 3.9 | 99.2 | <0.05 | <0.05 | <0.05 | 0.06 | 0.21 | 0.12 | 0.39 |
| A | TS | 0.2% | I | 40 | 3.9 | 99.7 | <0.05 | <0.05 | <0.05 | 0.05 | 0.24 | 0.13 | 0.42 |
| B | TS | 0.0% | U | 40 | 4.3 | 99.3 | <0.05 | <0.05 | <0.05 | <0.05 | 0.26 | 0.41 | 0.67 |
| C | TS | 0.03% | U | 40 | 3.9 | 99.3 | <0.05 | <0.05 | <0.05 | 0.05 | 0.17 | 0.21 | 0.43 |
| D | TS | 0.05% | U | 40 | 3.9 | 99.2 | <0.05 | <0.05 | <0.05 | 0.06 | 0.21 | 0.24 | 0.51 |
| E | TS | 0.10% | U | 40 | 3.9 | 99.3 | <0.05 | <0.05 | <0.05 | 0.05 | 0.19 | 0.10 | 0.34 |
| B | NTS | 0.0% | — | — | 4.6 | 99.3 | <0.05 | <0.05 | <0.05 | <0.05 | <0.05 | 0.07 | 0.07 |

[1] The actual RRT for the 0.56 RRT peak is 0.50 RRT
[2] The actual RRT for the 0.80 RRT peak is 0.78 RRT

TABLE 7

Day 56

| Solution | TS or NTS | Citrate Buffer | U or I | Storage Temp (° C.) | pH | LC (%) | HNO (%) | DHM (%) | THO (%) | 0.56 RRT[1] (%) | 0.80 RRT[2] (%) | PHM (%) | Total Impurity (%) |
|---|---|---|---|---|---|---|---|---|---|---|---|---|---|
| Commercial | — | Yes | U | 25 | 4.0 | 97.3 | <0.05 | <0.05 | <0.05 | <0.05 | <0.05 | 0.45 | 0.45 |
| Commercial | — | Yes | I | 25 | 4.0 | 100.3 | <0.05 | <0.05 | <0.05 | <0.05 | 0.05 | 0.45 | 0.50 |
| A | TS | 0.2% | U | 25 | 3.9 | 100.0 | <0.05 | <0.05 | <0.05 | <0.05 | 0.16 | 0.08 | 0.24 |
| A | TS | 0.2% | I | 25 | 3.8 | 99.9 | <0.05 | <0.05 | <0.05 | <0.05 | 0.17 | 0.08 | 0.25 |
| B | TS | 0.0% | U | 25 | 4.6 | 98.9 | <0.05 | <0.05 | <0.05 | <0.05 | 0.22 | 0.35 | 0.57 |
| C | TS | 0.03% | U | 25 | 3.9 | 99.5 | <0.05 | <0.05 | <0.05 | <0.05 | 0.18 | 0.20 | 0.38 |
| D | TS | 0.05% | U | 25 | 4.0 | 98.9 | <0.05 | <0.05 | <0.05 | <0.05 | 0.21 | 0.18 | 0.39 |
| E | TS | 0.10% | U | 25 | 3.8 | 98.6 | <0.05 | <0.05 | <0.05 | <0.05 | 0.15 | 0.07 | 0.22 |
| Commercial | — | Yes | U | 30 | 4.0 | 98.9 | <0.05 | <0.05 | <0.05 | <0.05 | 0.06 | 0.46 | 0.52 |
| Commercial | — | Yes | I | 30 | 4.0 | 99.8 | <0.05 | <0.05 | <0.05 | <0.05 | 0.06 | 0.46 | 0.52 |
| A | TS | 0.2% | U | 30 | 3.9 | 99.1 | <0.05 | <0.05 | <0.05 | <0.05 | 0.16 | 0.08 | 0.24 |
| A | TS | 0.2% | I | 30 | 3.9 | 99.7 | <0.05 | <0.05 | <0.05 | <0.05 | 0.17 | 0.09 | 0.26 |
| B | TS | 0.0% | U | 30 | 4.4 | 99.8 | <0.05 | <0.05 | <0.05 | <0.05 | 0.19 | 0.32 | 0.51 |
| C | TS | 0.03% | U | 30 | 4.0 | 98.9 | <0.05 | <0.05 | <0.05 | <0.05 | 0.21 | 0.21 | 0.42 |
| D | TS | 0.05% | U | 30 | 3.9 | 99.2 | <0.05 | <0.05 | <0.05 | <0.05 | 0.30 | 0.25 | 0.55 |
| E | TS | 0.10% | U | 30 | 3.9 | 99.2 | <0.05 | <0.05 | <0.05 | <0.05 | 0.14 | 0.07 | 0.21 |
| Commercial | — | Yes | U | 40 | 4.0 | 99.3 | <0.05 | <0.05 | <0.05 | <0.05 | 0.11 | 0.49 | 0.60 |
| Commercial | — | Yes | I | 40 | 4.0 | 98.0 | <0.05 | <0.05 | <0.05 | <0.05 | 0.12 | 0.49 | 0.61 |
| A | TS | 0.2% | U | 40 | 3.9 | 98.5 | <0.05 | <0.05 | <0.05 | <0.05 | 0.23 | 0.13 | 0.36 |
| A | TS | 0.2% | I | 40 | 3.9 | 99.2 | <0.05 | <0.05 | <0.05 | <0.05 | 0.25 | 0.15 | 0.40 |
| B | TS | 0.0% | U | 40 | 4.2 | 98.8 | <0.05 | <0.05 | <0.05 | <0.05 | 0.29 | 0.38 | 0.67 |
| C | TS | 0.03% | U | 40 | 3.9 | 98.3 | <0.05 | <0.05 | <0.05 | 0.05 | 0.30 | 0.31 | 0.66 |
| D | TS | 0.05% | U | 40 | 3.9 | 99.1 | <0.05 | <0.05 | <0.05 | <0.05 | 0.22 | 0.21 | 0.43 |
| E | TS | 0.10% | U | 40 | 3.9 | 98.7 | <0.05 | <0.05 | <0.05 | <0.05 | 0.22 | 0.13 | 0.35 |
| B | NTS | 0.0% | — | — | 4.6 | 99.0 | <0.05 | <0.05 | <0.05 | <0.05 | 0.07 | 0.07 | 0.14 |

[1] The actual RRT for the 0.56 RRT peak is 0.50 RRT
[2] The actual RRT for the 0.80 RRT peak is 0.78 RRT

TABLE 8

Day 84

| Solution | TS or NTS | Citrate Buffer | U or I | Storage Temp (° C.) | pH | LC (%) | HNO (%) | DHM (%) | THO (%) | 0.56 RRT[1] (%) | 0.80 RRT[2] (%) | PHM (%) | Total Impurity (%) |
|---|---|---|---|---|---|---|---|---|---|---|---|---|---|
| Commercial | — | Yes | U | 25 | 4.0 | 101.3 | <0.05 | <0.05 | <0.05 | <0.05 | 0.08 | 0.49 | 0.57 |
| Commercial | — | Yes | I | 25 | 4.0 | 99.5 | <0.05 | <0.05 | <0.05 | <0.05 | 0.08 | 0.49 | 0.57 |
| A | TS | 0.2% | U | 25 | 3.9 | 99.1 | <0.05 | <0.05 | <0.05 | <0.05 | 0.23 | 0.11 | 0.34 |
| A | TS | 0.2% | I | 25 | 3.9 | 98.9 | <0.05 | <0.05 | <0.05 | <0.05 | 0.23 | 0.10 | 0.33 |
| B | TS | 0.0% | U | 25 | 4.3 | 99.7 | <0.05 | <0.05 | <0.05 | <0.05 | 0.30 | 0.46 | 0.76 |
| C | TS | 0.03% | U | 25 | 4.0 | 99.7 | <0.05 | <0.05 | <0.05 | <0.05 | 0.21 | 0.22 | 0.43 |
| D | TS | 0.05% | U | 25 | 3.9 | 99.3 | <0.05 | <0.05 | <0.05 | <0.05 | 0.22 | 0.20 | 0.42 |
| E | TS | 0.10% | U | 25 | 3.9 | 99.2 | <0.05 | <0.05 | <0.05 | <0.05 | 0.17 | 0.08 | 0.25 |
| Commercial | — | Yes | U | 30 | 4.0 | 98.4 | <0.05 | <0.05 | <0.05 | <0.05 | 0.09 | 0.49 | 0.58 |
| Commercial | — | Yes | I | 30 | 4.0 | 98.9 | <0.05 | <0.05 | <0.05 | <0.05 | 0.10 | 0.49 | 0.59 |
| A | TS | 0.2% | U | 30 | 3.9 | 99.3 | <0.05 | <0.05 | <0.05 | <0.05 | 0.21 | 0.10 | 0.31 |
| A | TS | 0.2% | I | 30 | 3.9 | 99.1 | <0.05 | <0.05 | <0.05 | <0.05 | 0.22 | 0.11 | 0.33 |
| B | TS | 0.0% | U | 30 | 4.3 | 99.3 | <0.05 | <0.05 | <0.05 | <0.05 | 0.31 | 0.46 | 0.77 |
| C | TS | 0.03% | U | 30 | 4.0 | 98.9 | <0.05 | <0.05 | <0.05 | 0.06 | 0.24 | 0.25 | 0.55 |
| D | TS | 0.05% | U | 30 | 3.9 | 99.1 | <0.05 | <0.05 | <0.05 | <0.05 | 0.20 | 0.19 | 0.39 |
| E | TS | 0.10% | U | 30 | 3.9 | 97.8 | <0.05 | <0.05 | <0.05 | <0.05 | 0.20 | 0.12 | 0.32 |
| Commercial | — | Yes | U | 40 | 4.0 | 100.0 | <0.05 | <0.05 | <0.05 | <0.05 | 0.17 | 0.53 | 0.70 |
| Commercial | — | Yes | I | 40 | 4.0 | 99.2 | <0.05 | <0.05 | <0.05 | <0.05 | 0.17 | 0.53 | 0.70 |
| A | TS | 0.2% | U | 40 | 3.9 | 99.2 | <0.05 | <0.05 | <0.05 | 0.05 | 0.29 | 0.17 | 0.51 |
| A | TS | 0.2% | I | 40 | 3.9 | 98.1 | <0.05 | <0.05 | <0.05 | 0.05 | 0.29 | 0.21 | 0.55 |
| B | TS | 0.0% | U | 40 | 4.2 | 98.7 | <0.05 | <0.05 | <0.05 | <0.05 | 0.35 | 0.37 | 0.72 |
| C | TS | 0.03% | U | 40 | 3.9 | 98.6 | <0.05 | <0.05 | <0.05 | 0.07 | 0.35 | 0.39 | 0.81 |
| D | TS | 0.05% | U | 40 | 3.9 | 98.7 | <0.05 | <0.05 | <0.05 | 0.06 | 0.31 | 0.30 | 0.67 |
| E | TS | 0.10% | U | 40 | 3.9 | 99.6 | <0.05 | <0.05 | <0.05 | <0.05 | 0.27 | 0.20 | 0.47 |
| B | NTS | 0.0% | — | — | 4.5 | 100.5 | <0.05 | <0.05 | <0.05 | <0.05 | 0.12 | 0.09 | 0.21 |

[1]The actual RRT for the 0.56 RRT peak is 0.50 RRT
[2]The actual RRT for the 0.80 RRT peak is 0.78 RRT The appearance for all samples over the tested time period was clear, colorless, and without visible particulate matter. All pH values tested were within the expected specification of 3.5 to 5.5. As can be seen from Tables 3-8, both the terminally sterilized samples and the non-terminally sterilized samples of solution B (containing no citrate buffer) had a higher pH than solutions A and C-E and the commercial composition at each day and storage condition tested, further demonstrating that the absence of buffer gives the solution a pH closer to the natural physiological pH of cerebrospinal fluid than the solutions containing buffer (e.g. solutions A and C-E and the commercial compositions).

The level of known impurities (and in particular PHM), unknown impurities at 0.80 RRT, and total impurities for terminally sterilized solutions A-E were higher at each day tested as compared to the non-terminally sterilized sample of solution B (containing no citrate buffer), demonstrating that terminal sterilization of the hydromorphone HCl solutions adversely impacts stability of the solutions.

As compared to the commercial composition, terminally sterilized samples of solutions A-E all had lower levels of known impurities, and in particular PHM, at all days and storage conditions tested, with the exception of the terminally sterilized samples of solution B at day 3, 25° C. storage; and at day 28, 25° C. storage, both of which had similar levels of PHM as the corresponding commercial samples. Similarly, the levels of total impurities were less for terminally sterilized solutions A and C-E, as compared to the commercial compositions, at all days and time periods tested, with the exception of terminally sterilized samples of solution C at day 3, 30° C.; day 7, 30° C.; day 28, 25° C. and 30° C.; day 56, 40° C.; and day 84, 40° C., all of which had comparable levels of total impurities, as compared to the corresponding commercial composition. In contrast, the level of unknown impurities at 0.80 RRT was higher for terminally sterilized solutions A-E, as compared to the commercial composition.

Upon close review of the impurity data for day 3, an unidentified peak at RRT 0.80 was found that was greater than other impurity peaks and exceeded the ICH threshold for 7,7-dihydroxy-hydromorphone for all of the terminally sterilized samples for compositions A-E. All of the terminally sterilized samples had higher impurity levels at RRT 0.80 when compared to the commercial compositions as well as the non-terminally sterilized sample of solution B that was tested at this time point. Although this unknown peak was present in both the terminally sterilized and non-terminally sterilized solution B samples, as well as the commercial composition samples, there was a significant difference in the level of the impurity in the different samples; i.e., the unidentified impurity level was about 0.07%, <0.05%, or 0.21% for the 0.80 RRT peak for the commercial sample, the non-terminally sterilized sample of solution B, and the terminally sterilized sample of solution B, respectively. Thus, to further evaluate the effects of terminal sterilization on the product impurity profile, the commercial composition was terminally sterilized using the same protocol as for solutions A-E (i.e., 20 minutes at 121.1° C.). The unknown impurity was found to be 0.17% at 0.80 RRT for the terminally sterilized commercial composition. Thus, the terminally sterilized sample of the commercial composition and of solution B both had around a 0.2% level of the 0.80 RRT impurity, while the non-terminally sterilized commercial composition and non-terminally sterilized solution B had around a 0.05% level of the 0.80 RRT impurity. This suggests that the commercial composition was aseptically filled rather than terminally sterilized.

According to ICH guidelines, for the designed dosage of hydromorphone HCl intrathecal injection, the qualifying threshold for unknown impurities is 0.20%. To control the levels of the 0.80 RRT impurity to lower than the qualification threshold, it is preferable that the solutions of the present disclosure be aseptically processed and not terminally sterilized.

Example 10

Particulate Profile of Terminally Sterilized Hydromorphone Hydrochloride Solutions Under Varying Storage Conditions Over Time Solution A and the commercial composition from Example 8 were stored inverted under varying storage conditions and evaluated over 8 weeks for particulate formation to determine whether the container (vial) closure system (i.e., amber glass 20 cc vials with rubber 20 cc vial stoppers and flip top aluminum crimp) used in Example 8 to prepare the vials containing hydromorphone HCl affected solution quality. Particulates levels were also tested at day 0 for the commercial composition and both the terminally sterilized and non-terminally sterilized samples of solution A. The results are set forth in Table 8.

TABLE 9

| | | Particulate Data | | | |
|---|---|---|---|---|---|
| Solution | TS or NTS | Storage Conditions | Time Tested | 10 μm | 25 μm |
| A | TS | n/a | Day 0 | 430 | 20 |
| A | NTS | n/a | Day 0 | 320 | 20 |
| A | TS | 25° C./60% RH | Day 3 | 450 | 20 |
| A | TS | 30° C./65% RH | Day 3 | 550 | 10 |
| A | TS | 40° C./75% RH | Day 3 | 290 | 10 |
| A | TS | 25° C./60% RH | Day 7 | 910 | 20 |
| A | TS | 30° C./65% RH | Day 7 | 790 | 20 |
| A | TS | 40° C./75% RH | Day 7 | 930 | 30 |
| A | TS | 25° C./60% RH | Week 2 | 600 | 30 |
| A | TS | 30° C./65% RH | Week 2 | 430 | 60 |
| A | TS | 40° C./75% RH | Week 2 | 180 | 20 |
| A | TS | 25° C./60% RH | Week 4 | 400 | 10 |
| A | TS | 30° C./65% RH | Week 4 | 660 | 10 |
| A | TS | 40° C./75% RH | Week 4 | 610 | 60 |
| A | TS | 25° C./60% RH | Week 8 | 960 | 20 |
| A | TS | 30° C./65% RH | Week 8 | 1140 | 40 |
| A | TS | 40° C./75% RH | Week 8 | 1450 | 50 |
| Commercial | NTS | n/a | Day 0 | 860 | 10 |
| Commercial | NTS | 25° C./60% RH | Day 3 | 1310 | 20 |
| Commercial | NTS | 30° C./65% RH | Day 3 | 800 | 0 |
| Commercial | NTS | 40° C./75% RH | Day 3 | 1000 | 10 |
| Commercial | NTS | 25° C./60% RH | Day 7 | 730 | 10 |
| Commercial | NTS | 30° C./65% RH | Day 7 | 610 | 0 |
| Commercial | NTS | 40° C./75% RH | Day 7 | 500 | 0 |
| Commercial | NTS | 25° C./60% RH | Week 2 | 440 | 0 |
| Commercial | NTS | 30° C./65% RH | Week 2 | 440 | 0 |
| Commercial | NTS | 40° C./75% RH | Week 2 | 300 | 0 |
| Commercial | NTS | 25° C./60% RH | Week 4 | 410 | 10 |
| Commercial | NTS | 30° C./65% RH | Week 4 | 190 | 0 |
| Commercial | NTS | 40° C./75% RH | Week 4 | 460 | 0 |
| Commercial | NTS | 25° C./60% RH | Week 8 | 920 | 40 |
| Commercial | NTS | 30° C./65% RH | Week 8 | 900 | 0 |
| Commercial | NTS | 40° C./75% RH | Week 8 | 650 | 0 |

The amount of particulates having a size of 10 μm or greater and 25 μm or greater that were present in each solution was determined using the Light Obscuration Particle Count Test described in USP 788.

As can be seen from Table 9, solution A had from 180 to 1450 particulates 10 μm or greater in size and from 10 to 60 particulates 25 μm or greater in size over the course of the 8 week experiment, while the commercial composition had from 190 to 1310 particulates 10 μm or greater in size, and from 0 to 40 particulates 25 μm or greater in size. The USP limits for this testing for 10 μm and 25 μm sized particulates is 6000 and 600, respectively. Thus, the container closure system used to prepare the vials in Example 8 did not adversely impact the levels of particulates in the product.

Example 11

Composition Profile of Hydromorphone Hydrochloride Solution with 0% Buffer Under Varying Storage Conditions Over Time The impurity profile and stability of 10 mg/mL hydromorphone HCl solutions stored under standard storage conditions (20° C./60% RH) or accelerated storage conditions (40° C./75% RH) was determined at various time points up to 36 months (standard storage) or 6 months (accelerated storage).

A hydromorphone HCl solution containing 0% buffer was prepared and filtered as described in Example 8. The solution was used to fill round amber 20 mL vials (available from The Glass Group, Inc., DSM Material No. 311398). A 20 mm barrier faced stopper (available from West, DSM Material No. 006262) and 20 mm flip-off seal (available from West, DSM Material No. 005786) were used as the container closure system. The container closure system complied with USP 661 monograph requirements. The filled containers were not terminally sterilized.

The appearance of the solutions was visually inspected to verify that the solutions were clear, colorless, and essentially free of visible contaminants. The percent label claim, level of related substances and impurities, level of particulate matter, level of bacterial endotoxins, and sterility were assessed to determine if the solutions complied with USP or European Pharmacopoeia (EP) standards at the time periods tested. pH was also tested. The results are set forth in Tables 10 and 11 below:

TABLE 10

| Stability at 25° C./60% RH | | | | | | | | | |
|---|---|---|---|---|---|---|---|---|---|
| | | Time Period (Months) | | | | | | | |
| Attribute | Specification/Requirement | 0 | 3 | 6 | 9 | 12 | 18 | 24 | 36 |
| Appearance | Clear, colorless, and essentially free of visible contaminants | X | X | X | X | X | X | X | X |
| Label claim | 98.0%-101.0% on dried basis (USP) | X | X | X | X | X | X | X | X |
| Related Substances/ Impurities | Total Impurities: NMT 0.5% (EP) | X | X | X | X | X | X | X | X |

TABLE 10-continued

Stability at 25° C./60% RH

| | | Time Period (Months) | | | | | | | |
|---|---|---|---|---|---|---|---|---|---|
| Attribute | Specification/Requirement | 0 | 3 | 6 | 9 | 12 | 18 | 24 | 36 |
| pH | 3.5-5.0 | X | X | X | X | X | X | X | X |
| Particulate Matter | 10 μm: 6000<br>25 μm: 600<br>(USP 788)[1] | X | NT | NT | NT | X | NT | X | X |
| Bacterial Endotoxin (EU/g) | NMT 0.7 EU/g (USP 85) | X | NT | NT | NT | X | NT | X | X |
| Sterility | Total aerobic microbial count<br>Total combined molds and yeasts count (USP) | X | NT | NT | NT | X | NT | X | X |

X = requirements met; NT = not tested; NMT = not more than
[1]Particulate matter was evaluated using the method described in USP 788, General Method entitled "Determination of Particulate Matter by Electronic Particle Counting System".

TABLE 11

Stability at 40° C./75% RH

| | | Time Period (Months) | | |
|---|---|---|---|---|
| Attribute | Specification/Requirements | 1 | 3 | 6 |
| Appearance | Clear, colorless, and essentially free of visible contaminants | X | X | X |
| Label claim | 98.0%-101.0% on dried basis (USP) | X | X | X |
| Related Substances/Impurities | Total Impurities: NMT 0.5% (EP) | X | X | X |
| pH | 3.5-5.0 | X | X | X |

X = requirements met;
NMT = not more than

As can be seen from Tables 10 and 11, the solutions met the requirements for appearance, label claim, impurity levels, pH, particulate matter, bacterial endotoxin levels, and sterility under both standard storage conditions and accelerated storage conditions at all time periods tested.

Example 12

Impurity Profile of Hydromorphone Hydrochloride Solution with 0% Buffer Under Varying Storage Conditions Over Time The impurity profile and stability of 10 mg/mL hydromorphone HCl solutions stored under 25°, 30° C., or 40° was determined at various time points up to 84 days.

A hydromorphone HCl solution containing 0% buffer was prepared, filtered, and packaged into vials as described in Example 11, except was not sparged during preparation to remove oxygen. The filled containers were not terminally sterilized.

The pH, percent label claim, and level of impurities were tested at time 0 (i.e., the day the solutions were manufactured) and at 3, 7, 14, 28, 56, and 84 days post manufacture. Percent label claim and level of impurities were determined using HPLC, as described in Example 8. The results are set forth in Tables 12-14 below.

TABLE 12

Stability Data at 25° C.

| | Time Period (days) | | | | | | |
|---|---|---|---|---|---|---|---|
| Attribute | 0 | 3 | 7 | 14 | 28 | 56 | 84 |
| pH | 5.0 | 4.5 | 4.6 | 4.5 | 4.5 | 4.6 | 4.3 |
| Label claim (%) | 99.0 | 99.0 | 99.0 | 100.0 | 100.2 | 98.9 | 99.7 |
| HNO (%) | <0.05 | <0.05 | <0.05 | <0.05 | <0.05 | <0.05 | <0.05 |
| DHM (%) | <0.05 | <0.05 | <0.05 | <0.05 | <0.05 | <0.05 | <0.05 |
| THO (%) | <0.05 | <0.05 | <0.05 | <0.05 | <0.05 | <0.05 | <0.05 |
| 0.56 RRT (%) | <0.05 | <0.05 | <0.05 | <0.05 | 0.05 | <0.05 | <0.05 |
| 0.80 RRT (%) | <0.05 | 0.31 | 0.21 | 0.26 | 0.27 | 0.22 | 0.30 |
| PHM (%) | <0.05 | 0.49 | 0.43 | 0.46 | 0.49 | 0.35 | 0.46 |
| Total Impurity (%) | 0.00 | 0.80 | 0.64 | 0.72 | 0.81 | 0.57 | 0.76 |

TABLE 13

Stability Data at 30° C.

| | Time Period (days) | | | | | | |
|---|---|---|---|---|---|---|---|
| Attribute | 0 | 3 | 7 | 14 | 28 | 56 | 84 |
| pH | 5.0 | 4.5 | 4.5 | 4.5 | 4.4 | 4.4 | 4.3 |
| Label claim (%) | 99.0 | 97.2 | 98.8 | 100.6 | 99.6 | 99.8 | 99.3 |
| HNO (%) | <0.05 | <0.05 | <0.05 | <0.05 | <0.05 | <0.05 | <0.05 |
| DHM (%) | <0.05 | <0.05 | <0.05 | <0.05 | <0.05 | <0.05 | <0.05 |
| THO (%) | <0.05 | <0.05 | <0.05 | <0.05 | <0.05 | <0.05 | <0.05 |
| 0.56 RRT (%) | <0.05 | <0.05 | <0.05 | <0.05 | <0.05 | <0.05 | <0.05 |
| 0.80 RRT (%) | <0.05 | 0.26 | 0.19 | 0.22 | 0.24 | 0.19 | 0.31 |
| PHM (%) | <0.05 | 0.42 | 0.41 | 0.45 | 0.44 | 0.32 | 0.46 |
| Total Impurity (%) | 0.00 | 0.68 | 0.60 | 0.67 | 0.68 | 0.51 | 0.77 |

TABLE 14

Stability Data at 40° C.

| | Time Period (days) | | | | | | |
|---|---|---|---|---|---|---|---|
| Attribute | 0 | 3 | 7 | 14 | 28 | 56 | 84 |
| pH | 5.0 | 4.5 | 4.5 | 4.4 | 4.3 | 4.2 | 4.2 |
| Label claim (%) | 99.0 | 97.5 | 99.6 | 100.8 | 99.3 | 98.8 | 98.7 |
| HNO (%) | <0.05 | <0.05 | <0.05 | <0.05 | <0.05 | <0.05 | <0.05 |
| DHM (%) | <0.05 | <0.05 | <0.05 | <0.05 | <0.05 | <0.05 | <0.05 |
| THO (%) | <0.05 | <0.05 | <0.05 | <0.05 | <0.05 | <0.05 | <0.05 |
| 0.56 RRT (%) | <0.05 | <0.05 | <0.05 | <0.05 | <0.05 | <0.05 | <0.05 |

TABLE 14-continued

Stability Data at 40° C.

| Attribute | Time Period (days) | | | | | | |
|---|---|---|---|---|---|---|---|
| | 0 | 3 | 7 | 14 | 28 | 56 | 84 |
| 0.80 RRT (%) | <0.05 | 0.25 | 0.20 | 0.25 | 0.26 | 0.29 | 0.35 |
| PHM (%) | <0.05 | 0.42 | 0.42 | 0.45 | 0.41 | 0.38 | 0.37 |
| Total Impurity (%) | 0.00 | 0.67 | 0.62 | 0.70 | 0.67 | 0.67 | 0.72 |

As can be seen from Tables 12-14, the pH of solutions containing no buffer had only a small pH change at each storage temperature (only 0.7, 0.7, and 0.8 pH units at 25° C., 30° C., and 40° C. storage temperatures, respectively) over the time period tested. This indicates that buffer is not necessary to keep the pH stable over time, even at elevated storage temperatures.

As can be seen from Tables 12-14, there was also an initial jump in levels of PHM, unknown impurities (0.80 RRT), and total impurities from day 0 to day 3, while levels of PHM, unknown impurities (0.80 RRT), and total impurities remained relatively constant from day 3 to day 84. Without wishing to be bound to any particular theory, it is believed that this initial increase in impurity levels is the result of rapid degradation due to the presence of dissolved oxygen in the solutions and/or oxygen in the vial headspace. Once this oxygen is consumed, the rate of degradation decreases and impurity levels stabilize.

Example 13

In this example, levels of known and unknown impurities in various lots of hydromorphone HCl solutions (10 mg/ml) were tested over 6 months at various storage conditions. The hydromorphone HCl solutions contained no buffer. The results are set forth in Table 15 below.

TABLE 15

| Storage Conditions | % PHM | % Unknown Impurities | RRT | % Total Impurities | % 7,7 Dihydroxy-Hydromorphone |
|---|---|---|---|---|---|
| Lot 1 | | | | | |
| Initial | 0.2 | 0.07 | 0.81 | 0.3 | |
| | 0.2 | 0.07 | 0.81 | 0.3 | |
| | 0.2 | 0.06 | 0.81 | 0.3 | |
| 25° C./60% RH | | | | | |
| 2 month | 0.3 | 0.14 | 0.81 | 0.4 | |
| | | 0.00 | 0.87 | | |
| 3 month | 0.3 | 0.20 | 0.81 | 0.6 | |
| | | 0.06 | 0.87 | | |
| 6 month | 0.3 | 0.07 | 0.85 | 0.7 | 0.3 |
| 40° C./75% RH | | | | | |
| 1 month | 0.4 | 0.26 | 0.81 | 0.7 | |
| 3 month | 0.5 | 0.46 | 0.81 | 1.1 | |
| | | 0.07 | 0.87 | | |
| 6 month | 0.7 | 0.06 | 0.14 | 1.7 | 0.6 |
| | | 0.22 | 0.32 | | |
| | | 0.11 | 0.51 | | |
| | | 0.06 | 0.85 | | |
| | | 0.05 | 0.88 | | |
| 30° C./65% RH | | | | | |
| 2 month | 0.3 | 0.19 | 0.81 | 0.6 | |
| | | 0.05 | 0.87 | | |
| Lot 2 | | | | | |
| Initial | 0.2 | 0.07 | 0.81 | 0.3 | |
| | 0.2 | 0.07 | 0.81 | 0.3 | |
| | 0.2 | 0.06 | 0.81 | 0.3 | |
| 25° C./60% RH | | | | | |
| 2 month | 0.3 | 0.14 | 0.81 | 0.4 | |
| | | 0.00 | 0.87 | | |
| 3 month | 0.3 | 0.20 | 0.81 | 0.5 | |
| | | 0.06 | 0.87 | | |
| 6 month | 0.3 | 0.07 | 0.85 | 0.7 | 0.3 |
| 40° C./75% RH | | | | | |
| 1 month | 0.5 | 0.28 | 0.81 | 0.8 | |
| 3 month | 0.5 | 0.47 | 0.81 | 1.1 | |
| | | 0.07 | 0.87 | | |
| 6 month | 0.7 | 0.06 | 0.14 | 1.7 | 0.6 |
| | | 0.22 | 0.32 | | |
| | | 0.12 | 0.51 | | |
| | | 0.05 | 0.56 | | |
| 30° C./65% RH | | | | | |
| 2 month | 0.3 | 0.21 | 0.81 | 0.6 | |
| | | 0.05 | 0.87 | | |
| Lot 3 | | | | | |
| Initial | 0.2 | 0.06 | 0.81 | 0.3 | |
| | 0.2 | 0.06 | 0.81 | 0.3 | |
| | 0.2 | 0.05 | 0.81 | 0.3 | |
| 25° C./60% RH | | | | | |
| 2 month | 0.2 | 0.13 | 0.81 | 0.4 | |
| | | 0.05 | 0.87 | | |
| 3 month | 0.2 | 0.18 | 0.81 | 0.4 | |
| | | 0.05 | 0.87 | | |
| 6 month | 0.3 | 0.06 | 0.85 | 0.6 | 0.3 |
| 40° C./75% RH | | | | | |
| 1 month | 0.4 | 0.26 | 0.81 | 0.7 | |
| 3 month | 0.4 | 0.46 | 0.81 | 1 | |
| | | 0.07 | 0.87 | | |
| 6 month | 0.6 | 0.06 | 0.14 | 1.6 | 0.6 |
| | | 0.22 | 0.32 | | |
| | | 0.13 | 0.51 | | |
| | | 0.05 | 0.55 | | |
| 30° C./65% RH | | | | | |
| 2 month | 0.2 | 0.19 | 0.81 | 0.5 | |
| | | 0.06 | 0.87 | | |
| Lot 4 | | | | | |
| Initial | 0.2 | 0.06 | 0.81 | 0.3 | |
| | 0.2 | 0.06 | 0.81 | 0.3 | |
| | 0.2 | 0.05 | 0.81 | 0.3 | |
| 25° C./60% RH | | | | | |
| 2 month | 0.3 | 0.13, 0.05 | 0.81, 0.87 | 0.5 | |
| 3 month | 0.2 | 0.20, 0.06 | 0.81, 0.87 | 0.5 | |
| 6 month | 0.3 | 0.7 | 0.85 | 0.7 | |
| 40° C./75% RH | | | | | |
| 1 month | 0.4 | 0.27 | 0.81 | 0.7 | |
| 3 month | 0.5 | 0.49 | 0.81 | 1.1 | |
| | | 0.07 | 0.87 | | |
| 6 month | 0.6 | 0.05 | 0.14 | 1.6 | 0.6 |
| | | 0.22 | 0.32 | | |
| | | 0.13 | 0.51 | | |
| 30° C./65% RH | | | | | |
| 2 month | 0.3 | 0.19 | 0.81 | 0.5 | |
| | | 0.05 | 0.87 | | |

TABLE 15-continued

| Storage Conditions | % PHM | % Unknown Impurities | RRT | % Total Impurities | % 7,7 Dihydroxy-Hydromorphone |
|---|---|---|---|---|---|
| Lot 5 | | | | | |
| Initial | 0.2 | 0.00 | 0.81 | | 0.2 |
| | 0.1 | 0.00 | 0.81 | | 0.1 |
| | 0.1 | 0.00 | 0.81 | | 0.1 |
| 25° C./60% RH | | | | | |
| 3 month | 0.2 | 0.11 | 0.81 | 0.3 | |
| | | 0.00 | 0.87 | | |
| 6 month | 0.2 | ND | ND | 0.4 | 0.2 |
| 40° C./75% RH | | | | | |
| 1 month | 0.3 | 0.16 | 0.81 | 0.5 | |
| 2 month | | | | | |
| 3 month | 0.4 | 0.31 | 0.81 | 0.8 | |
| | | 0.06 | 0.87 | | |
| 6 month | 0.6 | 0.08 | 0.14 | 1.2 | 0.4 |
| | | 0.12 | 0.32 | | |
| 30° C./65% RH | | | | | |
| 2 month | 0.2 | 0.11 | 0.81 | 0.3 | |
| | | 0.00 | 0.87 | | |
| Lot 6 | | | | | |
| Initial | 0.2 | 0.00 | 0.81 | | 0.2 |
| | 0.1 | 0.00 | 0.81 | | 0.1 |
| | 0.1 | 0.00 | 0.81 | | 0.1 |
| 25° C./60% RH | | | | | |
| 3 month | 0.2 | 0.11 | 0.81 | 0.3 | |
| | | 0.00 | 0.87 | | |
| 6 month | 0.3 | ND | ND | 0.4 | 0.2 |
| 40° C./75% RH | | | | | |
| 1 month | 0.4 | 0.18 | 0.81 | 0.5 | |
| 3 month | 0.4 | 0.31 | 0.81 | 0.8 | |
| | | 0.05 | 0.87 | | |
| 6 month | 0.6 | 0.08 | 0.14 | 1.2 | 0.4 |
| | | 0.13 | 0.32 | | |
| 30° C./65% RH | | | | | |
| 2 month | 0.2 | 0.12 | 0.81 | 0.3 | |
| | | 0.00 | 0.87 | | |

PHM = pseudohydromorphone;
RRT is the RRT at which the unknown impurities were determined.

As can be seen from Table 15, there was not a significant increase in impurity levels, even after 6 months of storage under accelerated storage conditions (i.e., 40° C., 75% RH), indicating that the solutions should be stable after 2 years of storage under recommended storage conditions, even without buffer.

From the foregoing description, one skilled in the art can easily ascertain the essential characteristics of this disclosure, and without departing from the spirit and scope thereof, can make various changes and modifications of the disclosure to adapt it to various usages and conditions.

What is claimed is:

1. A sterile aqueous pharmaceutical solution for intrathecal delivery consisting essentially of:
hydromorphone hydrochloride in a concentration of 2.0 mg/mL to 25.0 mg/mL, wherein the sterile solution is free of buffer and other additives, and wherein the other additives are selected from the group consisting of an active pharmaceutical ingredient other than hydromorphone or a pharmaceutically acceptable salt thereof, an acid, a pH adjuster, a preservative, a polymeric material, an emulsifier, a lubricant, an antioxidant, a suspending agent, an excipient other than water, a diluent, an oil, a surfactant, saline, a solvent, a metal salt, a mineral a vitamin, a sterilizer, a stabilizer, and combinations thereof, wherein the solution contains less than 0.15 wt % of pseudohydromorphone, less than 0.05 wt % of hydromorphone N-oxide, less than 0.05 wt % of dihydromorphine, and less than 0.05 wt % of 6-β-tetrahydrooripavine after storage for at least 3 months, and wherein at a 0.80 relative retention rate the sterile aqueous pharmaceutical solution is between 0.21 and 0.30 at a time range of between 7 and 84 days, and wherein the solution is prepared by:
(i) combining hydromorphone, a pharmaceutically acceptable salt thereof, or combinations thereof with sterile water in the absence of buffer and/or other additives and dissolving the hydromorphone and/or the pharmaceutically acceptable salt thereof to form the solution;
(ii) sparging the sterile water with an inert gas prior to combining with the hydromorphone and/or the pharmaceutically acceptable salt thereof;
(iii) sparging the resulting solution after the hydromorphone and/or the pharmaceutically acceptable salt thereof, is dissolved in sterile water and/or sparging after the concentration of the hydromorphone and/or the pharmaceutically acceptable salt thereof has been adjusted;
(iv) optionally holding under the blanket of inert gas, argon or nitrogen and prior to inserting the solution into a container and/or adding or injecting the inert gas into the headspace of the container to further purge oxygen therefrom;
(v) aseptically filtering the solution and;
optionally further comprising aseptically filling a container selected from the group consisting of an ampoule, a vial, and a syringe with the solution.

2. The solution of claim 1, wherein the pH of the solution is from about 4 to about 5 after storage for at least 3 months.

3. The solution of claim 1, wherein the solution is stored at about 25° C. and about 60% relative humidity, at about 30° C. and about 65% relative humidity, or at about 40° C. and about 75% relative humidity.

4. A pharmaceutical composition for intrathecal delivery consisting essentially of:
a sterile solution of hydromorphone and water, wherein the sterile solution is free of buffer and other additives, and wherein the other additives are selected from the group consisting of an active pharmaceutical ingredient other than hydromorphone or a pharmaceutically acceptable salt thereof, an acid, a pH adjuster, a preservative, a polymeric material, an emulsifier, a lubricant, an antioxidant, a suspending agent, an excipient other than water, a diluent, an oil, a surfactant, saline, a solvent, a metal salt, a mineral, a vitamin, a sterilizer, a stabilizer, and combinations thereof; and wherein the solution contains less than 0.15 wt % of pseudo-hydromorphone, less than 0.05 wt % of hydromorphone N-oxide, less than 0.05 wt % of dihydromorphine, less than 0.05 wt % of 6-β-tetrahydrooripavine after storage for at least 3 months and wherein the solution is prepared by:
i. combining hydromorphone, a pharmaceutically acceptable salt thereof, or combinations thereof with sterile water in the absence of buffer and/or other additives and dissolving the hydromorphone and/or the pharmaceutically acceptable salt thereof to form the solution;

ii. sparging the sterile water with an inert gas prior to combining with the hydromorphone and/or the pharmaceutically acceptable salt thereof;

iii. sparging the resulting solution after the hydromorphone and/or the pharmaceutically acceptable salt thereof, is dissolved in sterile water and/or sparging after the concentration of the hydromorphone and/or the pharmaceutically acceptable salt thereof has been adjusted;

iv. optionally holding under the blanket of inert gas, argon or nitrogen and prior to inserting the solution into a container and/or adding or injecting the inert gas into the headspace of the container to further purge oxygen therefrom;

v. aseptically filtering the solution and;

optionally further comprising aseptically filling a container selected from the group consisting of an ampoule, a vial, and a syringe with the solution.

5. The composition of claim 4, wherein the pH of the solution is from about 4 to about 5 after storage for at least 3 months.

6. The composition of claim 4, wherein the solution is stored at about 25° C. and about 60% relative humidity, at about 30° C. and about 65% relative humidity, or at about 40° C. and about 75% relative.

7. The solution of claim 1, wherein the solution is free of ascorbic acid, ascorbyl palmitate, butylated hydroxyanisole, butylated hydroxytoluene, hypophosphorous acid, monothioglycerol, sodium ascorbate, sodium formaldehyde sulfoxylate, sodium metabisulfite, sodium bisulfate, vitamin E, vitamin E derivatives, propyl gallate, or combinations thereof.

8. The solution of claim 7, wherein the solution is free of sodium bisulfate.

9. The solution of claim 1, wherein the solution is free of added hydrochloric acid, sodium hydroxide, or combinations thereof.

10. The composition of claim 4, wherein the solution is free of ascorbic acid, ascorbyl palmitate, butylated hydroxyanisole, butylated hydroxytoluene, hypophosphorous acid, monothioglycerol, sodium ascorbate, sodium formaldehyde sulfoxylate, sodium metabisulfite, sodium bisulfate, vitamin E, vitamin E derivatives, propyl gallate, or combinations thereof.

11. The composition of claim 10, wherein the solution is free of sodium bisulfate.

12. The composition of claim 4, wherein the solution is free of added hydrochloric acid, sodium hydroxide, or combinations thereof.

13. The composition of claim 4, wherein the solution is free of an additive that leads to an allergic response or granuloma formulation.

14. A sterile aqueous pharmaceutical solution for intrathecal delivery consisting of hydromorphone hydrochloride in a concentration of 2.0 mg/mL to 25.0 mg/mL, wherein the solution is free of buffer and other additives, and wherein the other additives are selected from the group consisting of an active pharmaceutical ingredient other than hydromorphone or a pharmaceutically acceptable salt thereof, an acid, a pH adjuster, a preservative, a polymeric material, an emulsifier, a lubricant, an antioxidant, a suspending agent an excipient other than water, a diluent, an oil, a surfactant, saline, a solvent, a metal salt, a mineral a vitamin, a sterilizer, a stabilizer, and combinations thereof, wherein, the solution contains less than 0.15 wt % of pseudohydromorphone, less than 0.05 wt % of hydromorphone N-oxide, less than 0.05 wt % of dihydromorphine, and less than 0.05 wt % of 6-β-tetrahydrooripavine after storage for at least 3 months, wherein the solution is prepared by:

(i) combining hydromorphone, a pharmaceutically acceptable salt thereof, or combinations thereof with sterile water in the absence of buffer and/or other additives and dissolving the hydromorphone and/or the pharmaceutically acceptable salt thereof to form the solution;

(ii) sparging the sterile water with an inert gas prior to combining with the hydromorphone and/or the pharmaceutically acceptable salt thereof;

(iii) sparging the resulting solution after the hydromorphone and/or the pharmaceutically acceptable salt thereof, is dissolved in sterile water and/or sparging after the concentration of the hydromorphone and/or the pharmaceutically acceptable salt thereof has been adjusted;

(iv) optionally holding under the blanket of inert gas, argon or nitrogen and prior to inserting the solution into a container and/or adding or injecting the inert gas into the headspace of the container to further purge oxygen therefrom;

(v) aseptically filtering the solution and;

optionally further comprising aseptically filling a container selected from the group consisting of an ampoule, a vial, and a syringe with the solution; and the solution has an unexpected advantage over intrathecal hydromorphone hydrochloride solutions containing buffers and other additives that can lead to allergic responses or toxicity complications.

* * * * *